United States Patent
Haas et al.

(10) Patent No.: US 10,413,511 B2
(45) Date of Patent: Sep. 17, 2019

(54) LIPOSOMAL FORMULATIONS OF LIPOPHILIC COMPOUNDS

(75) Inventors: Heinrich Haas, München (DE); Ursula Fattler, Oberwil (CH)

(73) Assignee: SynCore Biotechnology Co., Ltd., I-Lan (TW)

(*) Notice: Subject to any disclaimer, the term of this patent is extended or adjusted under 35 U.S.C. 154(b) by 766 days.

(21) Appl. No.: 13/697,906

(22) PCT Filed: May 20, 2011

(86) PCT No.: PCT/EP2011/058275
§ 371 (c)(1),
(2), (4) Date: Jun. 21, 2013

(87) PCT Pub. No.: WO2011/144745
PCT Pub. Date: Nov. 24, 2011

(65) Prior Publication Data
US 2013/0259922 A1    Oct. 3, 2013

Related U.S. Application Data

(60) Provisional application No. 61/347,222, filed on May 21, 2010.

(30) Foreign Application Priority Data

May 21, 2010  (EP) ..................................... 10163643

(51) Int. Cl.
*A61K 9/127* (2006.01)
*A61K 31/337* (2006.01)

(52) U.S. Cl.
CPC .......... *A61K 9/1278* (2013.01); *A61K 9/1272* (2013.01); *A61K 31/337* (2013.01)

(58) Field of Classification Search
CPC .................................................... A61K 9/127
See application file for complete search history.

(56) References Cited

U.S. PATENT DOCUMENTS 4,229,360 A   10/1980   Schneider et al.
4,247,411 A    1/1981   Vanlerberghe et al.
(Continued)

FOREIGN PATENT DOCUMENTS

CN    101444514 A    6/2009
EP       1393719 A1    3/2004
(Continued)

OTHER PUBLICATIONS

International Search Report dated Jan. 18, 2012, by the European Patent Office as the International Searching Authority in International Patent Application No. PCT/EP2011/058275.
(Continued)

*Primary Examiner* — Gollamudi S Kishore
(74) *Attorney, Agent, or Firm* — Lee & Hayes, P.C.

(57) ABSTRACT

The present invention relates to the preparation of liposomes with enhanced loading capacity for pharmaceutically and/or diagnostically active agents and/or cosmetic agents which are substantially solubilized by the liposomal membranes, to liposome dispersions with enhanced stability with respect to release of the active agent and/or cosmetic agent from the liposomes obtainable by the process, and to pharmaceutical or cosmetic compositions comprising said stabilized liposome dispersions. The preparation may involve dehydration and rehydration steps of liposome dispersions which may be carried out by spray drying.

13 Claims, 2 Drawing Sheets

(56) References Cited

U.S. PATENT DOCUMENTS

Figure 1:
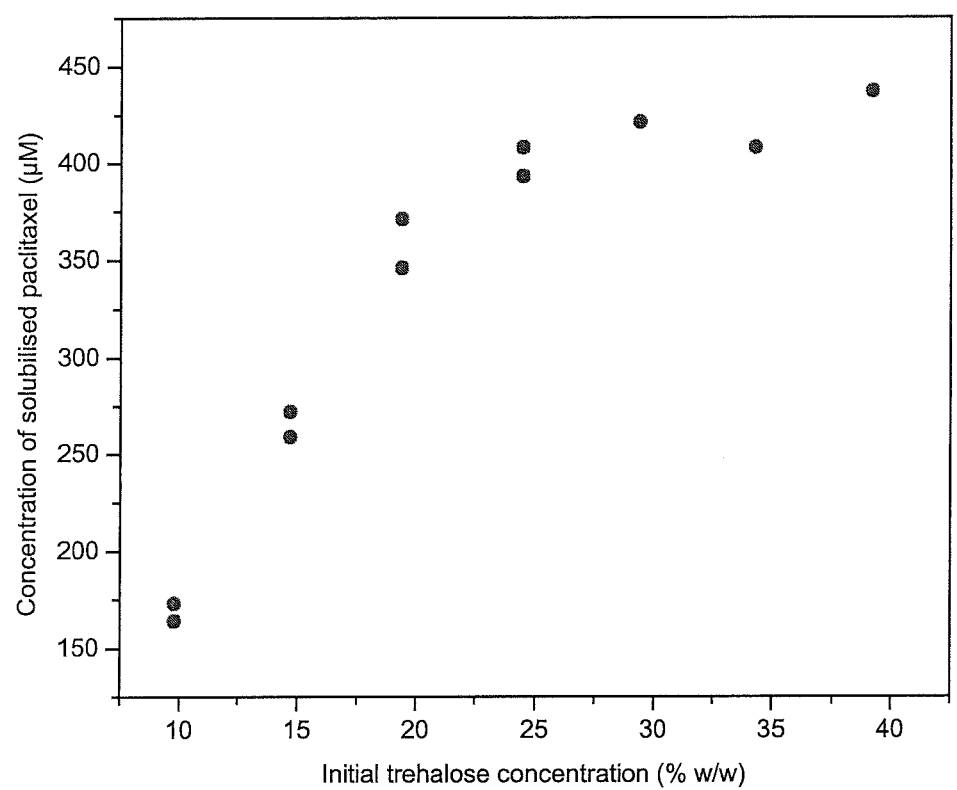

| | | | |
|---|---|---|---|
| 4,880,635 A | | 11/1989 | Janoff et al. |
| 4,883,665 A | | 11/1989 | Miyazima et al. |
| 4,895,719 A | | 1/1990 | Radhakrishnan et al. |
| 5,049,392 A | * | 9/1991 | Weiner .................. A61K 9/1278 264/4.1 |
| 5,089,181 A | | 2/1992 | Hauser |
| 5,094,854 A | | 3/1992 | Ogawa et al. |
| 5,498,633 A | | 3/1996 | Santaniello et al. |
| 7,811,602 B2 | * | 10/2010 | Cullis .................. A61K 9/1272 424/450 |
| 2005/0112065 A1 | * | 5/2005 | Drummond .......... A61K 9/1272 424/9.321 |
| 2005/0202076 A1 | * | 9/2005 | Mundus ............... A61K 9/1272 424/450 |
| 2008/0107722 A1 | * | 5/2008 | Tardi .................... A61K 9/1278 424/450 |
| 2008/0213345 A1 | * | 9/2008 | Hu ....................... A61K 9/0019 424/450 |
| 2010/0316696 A1 | * | 12/2010 | Wiggenhorn ........ A61K 9/1277 424/450 |
| 2013/0052259 A1 | * | 2/2013 | Barenholz ............ A61K 9/1271 424/450 |

FOREIGN PATENT DOCUMENTS

| | | | |
|---|---|---|---|
| EP | 1 920 765 | * | 7/2006 |
| EP | 1795184 A1 | | 6/2007 |
| JP | 2-1404 A | | 1/1990 |
| JP | 3026271 U | | 7/1996 |
| JP | 2001-515853 A | | 9/2001 |
| JP | 2006-516650 A | | 7/2006 |
| JP | 4786105 B2 | | 10/2011 |
| JP | 2013-508315 A | | 3/2013 |
| WO | 96/08235 A1 | | 3/1996 |
| WO | 99/12523 A1 | | 3/1999 |
| WO | 01/05372 A2 | | 1/2001 |
| WO | 2007012191 A1 | | 2/2001 |
| WO | 01/56548 A2 | | 8/2001 |
| WO | 2004/002468 A1 | | 1/2004 |
| WO | 2004007492 A1 | | 1/2004 |
| WO | 2004048372 A1 | | 6/2004 |
| WO | 2004/069224 A2 | | 8/2004 |
| WO | 2005030767 A1 | | 4/2005 |
| WO | 2005/039533 A1 | | 5/2005 |
| WO | 2005051947 A1 | | 6/2005 |
| WO | WO2006050327 | | 5/2006 |
| WO | 2006/117220 A2 | | 11/2006 |
| WO | 2007/005754 A2 | | 1/2007 |
| WO | 2007/107305 A2 | | 9/2007 |
| WO | 2011/047689 A2 | | 4/2011 |

OTHER PUBLICATIONS

Written Opinion of the International Searching Authority dated Jan. 18, 2012, in corresponding International Patent Application No. PCT/EP2011/058275.

Campbell et al., "Influence of Cationic Lipids on the Stability and Membrane Properties of Paclitaxel-Containing Liposomes," Journal of Pharmaceutical Sciences, 2001, pp. 1091-1105, vol. 90, No. 8.

Lo et al., "Liposomes and disaccharides as carriers in spray-dried powder formulations of superoxide dismutase," Journal of Controlled Release, 2004, pp. 259-272, vol. 94.

DrugBank: Cefmenoxime, Accession No. DB00267 [URL: http://www.drugbank.ca/drugs/D800267].

Antonietti et al., "Vesicles and Liposomes: A Self-Assembly Principle Beyond Lipids," Adv. Mater., 2003, pp. 1323-1333, vol. 15, No. 16.

Bangham et al., "Diffusion of Univalent Ions Across the Lamellae of Swollen Phospholipids," J. Mol. Biol., 1965, pp. 238-252, vol. 1.

Cabral et al., "Preparation and Characterization of Liposomes Entrapping Allergenic Proteins," Brazilian Journal of Chemical Engineering, 2004, pp. 137-146, vol. 21, No. 2 Chemical.

De Gier, "Osmotic behavior and permeability properties of liposomes," Chemistry and Physics of Lipids, 1993, pp. 187-196, vol. 64.

Ertel et al., "Mechanical properties of vesicles," Biophys. J., 1993, pp. 426-434, vol. 64.

Goormaghtigh et al., "Density-Based Separation of Liposomes by Glycerol Gradient Centrifugation," Analytical Biochemistry, 1986, pp. 122-131, vol. 159.

Gregoriadis, "Engineering liposomes for drug delivery: progress and problems," Trends in Biotechnology, 1995, pp. 527-537, vol. 13.

Hallett et al., "Mechanical properties of vesicles," Biophys. J., 1993, pp. 435-442, vol. 64.

Huang et al., "Studies on Phosphatidylcholine Vesicles," The Journal of Biological Chemistry, 1971, pp. 2555-2560, vol. 246, No. 8.

Koppel, "Analysis of Macromolecular Polydispersity in Intensity Correlation Spectroscopy: The Methods of Cumulants," The Journal of Chemical Physics, 1972, pp. 4814-4820, vol. 57, No. 11.

New, "Preparation of liposomes," Liposomes: A Practical Approach, 1990, pp. 33-104, Oxford University Press Inc., New York, NY.

Translation of Russian Office Action dated Apr. 26, 2016 from Application Serial No. 2012155697/15(088146); 14 pages.

Moen, Helene: "Influence of osmotic stress on liposome size and morphology", Thesis for the degree Master of Pharmacy, 2008.

Russian Office Action dated Jan. 21, 2016 from Application Serial No. 2012155697/15(088146); 13 pages.

Canadian Office Action dated Jan. 10, 2017 for Canadian Application No. 2796806, a foreign corresponding to U.S. Appl. No. 13/697,906, 8 pages.

Feigner et al., "Enhanced gene delivery and mechanism studies with a novel series of cationic lipid formulations," Jan. 28, 1994, The Journal of Biological Chemistry, 269(4): 2550-2561.

Korean Office Action dated Jul. 27, 2017 for Korean Patent Application No. 10-2012-7030293, a foreign corresponding application of U.S. Appl. No. 13/697,906, 23 pages.

Ohtake et al, "Effects of trehalose on the phase behavior of DPPC-cholesterol unilamellar vesicles," Jan. 27, 2006, Biochimica et Biophysica Acta, 1758: 65-73.

* cited by examiner

LIPOSOMAL FORMULATIONS OF LIPOPHILIC COMPOUNDS

CROSS-REFERENCE TO PRIOR APPLICATIONS

This application is a National Stage of PCT/EP2011/058275, filed May 20, 2011, and designating the United States, which claims priority to European Patent Application No. 10163643.9, filed May 21, 2010, and to U.S. Provisional Patent Application No. 61/347,222, filed May 21, 2010, each hereby expressly incorporated by reference in its entirety.

FIELD OF THE INVENTION

The present invention relates to the preparation of liposomes with enhanced loading capacity for pharmaceutically and/or diagnostically active agents and/or cosmetic agents which are substantially solubilized by the liposomal membranes, to liposome dispersions with enhanced stability with respect to release of the active agent and/or cosmetic agent from the liposomes obtainable by the process, and to pharmaceutical or cosmetic compositions comprising said stabilized liposome dispersions. The preparation may involve dehydration and rehydration steps of liposome dispersions which may be carried out by spray drying.

BACKGROUND

Liposomes are artificial vesicular structures composed of single or multiple membranes enclosing an aqueous compartment. Most typically, liposome membranes are formed from lipid bilayers, but they can consist as well from other monomeric and polymeric amphiphilic compounds, including other types of amphiphiles, polymers and polypeptides (Antonietti and Forster 2003). Liposomes form spontaneously when lipids are dispersed in an aqueous environment under suitable conditions. Most liposomes are non-toxic, non-antigenic and biodegradable in character since they have the molecular characteristics of mammalian membranes. Lipophilic or amphiphilic drugs and compounds can be incorporated into the liposome membrane, hydrophilic drugs and compounds can be encapsulated in the aqueous cores of the liposomes.

In recent years liposomes have become an important tool in the pharmaceutical industry for the delivery of drugs (Gregoriadis 1995). Liposomes are capable of influencing pharmacokinetics by a sustained release of the drug to the body or reduce side effects by limiting the free concentration of a drug. By attaching ligands to the liposome or rendering their charge, liposomes facilitate a targeted delivery of drugs to a desired site of action. Beside the pharmaceutical use, liposomes are also frequently used for cosmetic products.

If liposomes are used for the administration of active agents within pharmaceutical or cosmetic use, it is important to control and optimize the loading efficacy of the active compound to the liposomal formulation and the stability of the liposomal formulation loaded with the active or cosmetic compound. The stability of the formulation is a crucial characteristic during manufacturing, storage and application of the formulation. In many cases physical or chemical stability of liposome products is limited, which has to be taken into account for planning of manufacturing processes (hold time), storage (shelf life stability) and application of the product (in-use stability).

For pharmaceutical application liposome formulations are often administered by injection. Thus the liposomes must be present in an aqueous phase under conditions suitable for intravenous (iv) or intraperitoneal (ip) administration.

Pharmaceutical liposome formulations are subjected to extremely stringent quality criteria. Most present liquid liposome products are not stable over a longer storage period, because they can undergo a variety of chemical and physical degradation processes. However, for pharmaceutical products it is desirable to have final formulations which are stable for at least six months to two years at room temperature or at refrigeration temperature. These factors restrict the use of liposomes as practical carriers of biologically active compounds. For liposomes, techniques for dehydration have been developed to meet these requirements.

Long term stability of liposome formulations is greatly enhanced when they are dehydrated and stored as dry rather than liquid formulations. Before injection, the dry liposome products have to be rehydrated in a suitable aqueous medium generating aqueous suspensions for administration. Because the stability of the rehydrated liposome formulations may again be limited by chemical and physical degradation processes, the increase of the in-use stability of said ready to use liposomal suspension is another important goal of pharmaceutical formulation technology.

A commonly used stabilization method for aqueous liposome suspensions by freeze-drying is described in U.S. Pat. Nos. 4,229,360 and 4,247,411. In the freeze-drying process, a liposomal suspension is frozen and subsequently subjected to reduced pressure, which leads to removal of the frozen water by sublimation. Usually, the aqueous suspension comprises an excipient, such as a sugar, to prevent or minimize defect formation induced by freezing and dehydration. The freeze-drying procedure results in liposomes in a protective matrix of excipient from which, after rehydration, the antecedent liquid product is to be obtained. As disclosed in U.S. Pat. No. 4,880,635 the liposomes can be protected from detrimental effects of the dehydration and rehydration steps by the presence of a protective sugar, not only on the outside, but also inside the liposome.

The spray-drying method, as for example disclosed in U.S. Pat. No. 5,089,181, provides an alternative process for preparing a stable dehydrated liposomal formulation. The process has been adapted from the food industry and employs the atomising of suspensions into small droplets by spraying said suspension, and the subsequent evaporation of the medium from the droplets at elevated temperatures. Like in the freeze drying process, the liposomal suspension may comprise an excipient, such as a sugar, to protect the liposomal membranes. In comparison to freeze-drying, the spray-drying process has considerable advantages with respect to large scale industrial application, because it enables larger manufacturing capacities at lower cost and with manageable technological efforts. However, the elevated temperatures involved in this method apply stress to the encapsulated active agent as well as to the lipid membranes.

To stabilize suspensions which comprise a water soluble drug encapsulated in liposomes for spray drying, U.S. Pat. No. 4,895,719 discloses to balance a high internal osmolarity generated by a high internal concentration of the soluble drug with an evenly high osmolarity of the surrounding medium.

To stabilize hydrophobic drugs in the aqueous phase of liposomes, WO 2007/005754 discloses the complexation of such drugs by cyclodextrins prior to encapsulation. The complexed hydrophobic drug is retained in the liposome at high concentrations, even in the presence of a transmembrane osmotic gradient caused by the cyclodextrin. However a stabilization for active agents embedded in the liposomal membrane is not disclosed.

The presence of solutes that are osmotically active, such as sugars or ions, inside or outside the liposomal membranes generates osmotic forces. The way how transmembrane osmotic gradients act on the structure and dynamics of biological membranes has been investigated in the literature, and models to describe phenomena like stress-strain relation and lysis have been proposed (Ertel, Marangoni et al. 1993; Hallett, Marsh et al. 1993). Briefly, the experiments by the authors and the accompanying analysis underline that swelling of liposomes at a given osmotic stress depends on their size. Swelling up to a size dependent critical yield point was described, at which lysis (leakage) occurred. Conditions under which liposomes are expected to reside in a consistently strained state were given.

With regard to the production of liposomes comprising a lipophilic drug that have an enhanced shelf live, WO 2004/002468 discloses the preparation of liposomes which comprise paclitaxel. The liposomes are formed in an aqueous buffer comprising trehalose, resulting in a liposomal suspension having the same osmolarity inside and outside the liposome. The aqueous liposomal suspension is subsequently dehydrated. The dehydration process may be carried out by freeze-drying or spray-drying. The application discloses several protocols for the freeze drying of said liposomal suspensions. After dehydration, the liposomal preparation can be rehydrated by the addition of water or an aqueous solution. The document does not provide comparative data on the in-use stability of liposomal preparations that were dehydrated by freeze-drying or by spray-drying prior to their rehydration.

In view of the described state of the art, the problem underlying the present invention was the preparation of liposomes, comprising at least one lipohilic active agent and/or cosmetic agent with a high agent to lipid ratio and with improved stability, especially regarding physical stability and release of the agent from the liposome. Especially the invention relates to the problem of providing a process for manufacturing said liposomal preparations that have an extended hold time during manufacturing and in-use stability, wherein the process involves a fast dehydration step.

Thus, the solution of the above problem is achieved according to the present invention by providing embodiments characterised in the claims and further depicted in the description of the invention.

SUMMARY OF THE INVENTION

The solution of the above problem is provided by liposome preparations where tensile stress on the liposome membranes is applied by osmotic forces and a process for preparing said liposomes.

Specifically, the solution is provided by a process for the preparation of a liposomal suspension in an aqueous phase with at least one active agent and/or cosmetic agent present in the liposomal membrane, wherein said suspension comprises at least one osmotically active substance in the aqueous phase, and wherein the osmolarity of the aqueous phase inside the liposomally encapsulated volume, $O_{in}$, is higher than the aqueous phase outside the liposomally encapsulated volume, $O_{out}$.

The liposomes are characterised by the presence of tensile stress on the liposome membranes (stressed liposomes). They can be obtained directly during liposome formation or at any processing step after liposome formation.

Stressed liposomes can be obtained by directly affecting the osmolarity of the aqueous phase inside and/or outside the liposomes or by changing membrane characteristics, such as molecular packing, of the liposome membrane where the liposomes are present in a medium of a given osmolarity.

Stressed liposomes can be prepared directly with the active agent and/or cosmetic agent present in the liposome membrane. Alternatively, stressed liposomes can be prepared without the agent, which is subsequently added to the liposomes.

An aspect of the invention relates to a process for the manufacture of a liposomal preparation comprising:
a) providing a first liposomal preparation comprising a suspension of liposomes in an aqueous phase, wherein the liposomes comprise at least one membrane, wherein the membrane encloses a liposomally encapsulated volume of the aqueous phase and the aqueous phase comprises at least one osmotically active substance and has an initial overall osmolarity, $O_1$, b) thereafter generating an osmolar gradient in the aqueous phase of said preparation wherein the osmolarity of the aqueous phase outside the liposomally encapsulated volume, $O_{out}$, is lower than the osmolarity of the aqueous phase inside the liposomally encapsulated volume, $O_{in}$, to yield a second (stressed) liposomal preparation,
c) optionally dehydrating the second (stressed) liposomal preparation to obtain a dehydrated preparation, and
d) optionally rehydrating the dehydrated preparation.

The liposomal preparation of step a) preferably comprises at least one active agent or cosmetic agent in the liposomal membrane. Alternatively, the agent may be added at a later stage of the manufacturing process.

Step b) can be performed by reducing the initial overall osmolarity, $O_1$, of the liposomal suspension derived from step a) to yield a stressed liposomal preparation with an overall osmolarity, $O_2$, which is lower than the osmolarity $O_1$.

Step b) may be performed by diluting the liposomal suspension derived from step a) with an aqueous medium having an osmolarity which is lower than $O_1$, or by dialysing the suspension against an aqueous medium with an osmolarity which is lower than $O_1$. In the most simple way, the liposomal suspension is diluted with water.

According to the general concept of the invention an osmolar gradient may be generated or altered at different stages during the manufacture of the liposome preparation. Also the osmolar gradient may be altered once or multiple times at several stages of the production process. This can possibly be achieved by the same or different procedures as described in the following. The production process of the liposomal preparation relates to all steps performed before the final application of the liposomal suspension.

Step b) of the inventive process may comprise the steps of:
b1) dehydrating the liposomal preparation in step a) to obtain a dehydrated liposomal preparation, and
b2) rehydrating said dehydrated liposomal preparation under conditions to yield a stressed liposomal preparation, preferably in an aqueous medium.

Preferably the dehydration is performed by spray drying of the liposomal suspension.

The invention also relates to compositions obtained or obtainable by the above processes.

Also the invention relates to a liposomal preparation comprising at least one active agent or a cosmetic agent in the liposomal membrane, wherein the liposomal membrane is under tensile stress.

More particularly, the invention relates to a liposomal preparation comprising at least one active agent or cosmetic agent in the liposomal membrane wherein the liposomes are present in a liquid phase with an osmolarity inside the liposomally encapsulated volume ($O_{in}$) which is higher than the osmolarity of the liquid phase outside of the liposomally encapsulated volume ($O_{out}$).

Surprisingly, the inventors have found that liposomal suspensions containing liposomes, whose liposomal membrane is under tensile stress, have an improved solubility for lipophilic compounds.

Thus the invention also relates to a process for manufacturing a liposomal preparation comprising at least one lipophilic drug or cosmetic compound, comprising the steps of:

i) providing a stressed liposomal preparation, comprising a suspension of liposomes in an aqueous phase, ii) incubating said stressed liposomal preparation with at least one lipophilic active agent or cosmetic agent, optionally in an unsolubilised form, and iii) optionally separating unsolubilised agent from the liposome preparation, preferably by filtration or centrifugation, iv) optionally dehydrating the incubated liposomal preparation, and v) optionally rehydrating the dehydrated liposomal preparation.

Stressed liposomes can be obtained by any of the above mentioned procedures. Most preferably, at least one osmotically active substance is present in the aqueous phase of the liposome suspension, wherein $O_{in}$ is higher than $O_{out}$.

The above mentioned active agent or cosmetic agent preferably has a low solubility in water.

The above mentioned active agent or cosmetic agent is lipophilic and preferably has a log P of greater than 1. More preferably the compound is a taxane, most preferably paclitaxel or a derivative thereof.

It has been surprisingly found that the loading efficacy of lipophilic, poorly water soluble compounds, such as paclitaxel, to liposome membranes can be improved, and the release of such compounds from the liposome membranes can be reduced, if the liposomal membrane is stressed, particularly, if a water-soluble osmotically active compound is comprised in the liposomally encapsulated aqueous phase at a higher concentration than outside of the liposomally encapsulated phase. The higher loading efficacy of the lipophilic compound to these liposomes compared to liposomes without a concentration gradient enables to manufacture formulations with higher molar ratio of compound/lipid, and to improve the stability of given formulations because the tendency to release the compound from the liposome is reduced.

Liposomes comprising a lipophilic agent in the membrane compartment are less prone to release of the compound to the aqueous medium if said osmolar gradient is present. The equilibrium fraction of said lipophilic substance in the aqueous medium is reduced. Accordingly the risk that the concentration of the lipophilic compound in the aqueous phase exceeds the solubility limit and precipitates is also reduced.

Moreover it has been surprisingly found that empty liposomes comprising the above described gradient have a higher loading capacity for lipophilic compounds, i.e. a higher molar amount of lipophilic compound is solubilised by the same amount of liposomes (as defined by molar amount of lipid) in comparison to liposomes without such gradient. This can be realized, for example, by exposure of the lipophilic compound to empty liposomes.

It has also been surprisingly found, that liposomal preparations obtained by rehydration of previously dehydrated liposomes have a homogeneous size distribution, as indicated by a low polydispersity index (PI). With regard to quality control, it is always desirable to obtain a homogeneous product, especially for pharmaceutical uses. Furthermore the liposome suspensions of the present invention exhibit a polydispersity index which remains substantially unchanged over a prolonged period of time. This indicates that the liposomes in the inventive suspensions do not form aggregates. Especially for intravenously administered liposomal suspensions, aggregates have to be avoided, because these aggregates may obstruct blood vessels and thus lead to embolies.

The present invention substantially improves the state of the art by providing a process for stabilizing lipophilic agents in the liposomal membranes of a liposomal preparation, as well as maintaining size and polydispersity of a rehydrated liposomal preparation. As a consequence, the in-use stability of a final preparation comprising liposomes with a lipophilic compound can be prolonged. Also the stability of said liposomes during the processing of such formulations can be prolonged.

In many cases the time period for processing the liquid formulations during manufacturing (hold time) of liposome formulations is limited due to the risk of undesired release of the agent from the liposomes. The invention reduces the risk of drug release, and therefore it enables continuous processing of liposomes during manufacturing for extended time scales and enables a more flexible design of the production process.

More specifically the invention enables the preparation of the above mentioned formulations by spray-drying instead of freeze-drying. In freeze drying the liposomes are frozen and thus stabilized directly after manufacturing, therefore the risk of release during manufacturing is low. In spray drying the liquid formulations encounter extended hold times in the liquid phase, because spraying of a given batch may take several hours or days. Because the invention enables to increase the stability of a given formulation, longer spraying sessions without interruption can be realised. Since spray-drying has a higher overall throughput compared to freeze-drying, large scale production is facilitated and production costs can be reduced, while product quality is maintained.

Further the risk of drug release and crystallization in the period between reconstitution of the dehydrated liposomal composition and administration to a patient (in-use stability) is reduced. Crystallization may promote formation of sub-visible particles which must not be present beyond certain limits in products for iv administration. In many cases, only an in-use stability of few hours is provided, which is an obstacle in clinical practice. Therefore, sufficient in-use stability is of great importance for practical application of such pharmaceutical or cosmetic products.

The preparation of liposomes frequently employs organic solvents, such as ethanol, which is usually found in dehydrated liposomal products, and accordingly in the rehydrated liposomal suspensions derived from it. This is especially the case for liposomal preparations which were dehydrated by freeze-drying (lyophilisation). However it is desirable for liposomal products used for application to humans to comprise as little organic solvent as possible. The present invention enables dehydration by spray-drying, which facilitates the removal of most or all residual organic solvent, while obtaining liposomes with a high stability.

While providing the above mentioned advantages, the invention can be practiced easily and is not cost intensive. It does neither require complicated technical devices, nor the addition of further ingredients to the above mentioned compositions. The osmotically active substances, which are used to practice the invention, are already known from liposomal compositions which are dehydrated as disclosed in U.S. Pat. No. 4,880,635 or WO 2004/002468.

Definitions

"About" in the context of amount values refers to an average deviation of maximum +/−20%, preferably +/−10% based on the indicated value. For example, an amount of about 30 mol % cationic lipid refers to 30 mol %+/−6 mol % and preferably 30 mol %+/−3 mol % cationic lipid with respect to the total lipid/amphiphile molarity.

"Active compound" or "active agent" refers to a compound or mixture of compounds, having a particular biological or physical activity based on which it is useful as an agent for the diagnosis, prevention, or treatment of a human or animal disease or condition. Therapeutic agents such as drug substances and diagnostic agents are important examples of active agents according to the present invention.

"Anhydrous density" of liposomes within the current invention means the mass of all compounds constituting said liposomes, including the compounds encapsulated by the liposomes, but excluding the mass of water comprised in such liposomes, divided by the volume of the liposome in an aqueous phase, based on the liposomal particle size $z_{average}$. In a very specific example, the anhydrous density of liposomes may refer to the mass of DOTAP, DOPC, paclitaxel, citric acid and trehalose comprised in a liposome, divided by the volume of the liposome in an aqueous phase. The anhydrous density liposomes can be determined by ultracentrifugation methods as disclosed in the examples.

"Aqueous medium", "aqueous liquid" or "aqueous phase" as used herein refers to a liquid material which comprises water. In some embodiments, the liquid material comprises at least 50% (w/w), at least 70% (w/w) or at least 90% (w/w) water. In other embodiments, the liquid material is free from organic solvents. The aqueous phase may contain one or several compounds. Thus, an aqueous dispersion, aqueous suspension and an emulsion in which the continuous phase is aqueous are also examples of aqueous liquids. An aqueous liquid which contains a colloidal material is hereinafter sometimes referred to as an aqueous colloidal dispersion or solution.

"Cationic" refers to an agent that has a net positive charge or positive zeta potential under the respective environmental conditions. In the present invention, it is referred to environmental conditions where the pH is in the range between 3 and 9, preferably between 5 and 8.

"Chemical stability" of the lipophilic compound refers to a significant change of it's original chemical structure, and is defined as about 5% activity change from the initial assay value (original compound), preferably about 2% or appearance of specific degradation products exceeding its acceptance criteria with respect to toxicological limits and safety aspects. For lipophilic compounds such as paclitaxel chemical stability can be defined by HPLC/LC MS/MS and typically means less than 5% degradation products of said compound. Typical degradation products of paclitaxel are e.g. Baccatinill, 7-Epi-Taxol etc. (Monography of Paclitaxel, USP26, [January-March 2003], USPC, Inc.).

"Cosmetic compound" refers to a compound which has an effect on the human skin or hair.

"Diagnostically active agent" or "diagnostic" refers to a pharmaceutically acceptable agent that can be used to visualise a biological property or state in a subject or sample by various methods. The visualisation can be used to make a diagnosis.

"Dehydration" or "dehydrate" refers to the process of withdrawing water from a composition. In some embodiments, water is withdrawn from the composition to a residual content of lower than about 10% (w/w), preferably lower than about 5% (w/w), based on the content of water present before the dehydration procedure.

"Encapsulated volume" or "encapsulated phase" refers to a volume which is enclosed by at least one liposome membrane. The volume may be enclosed by one membrane in unilamellar liposomes or several membranes in multilamellar liposomes. Thus the encapsulated phase represents the space inside of a liposome, whereas the volume outside the liposomally encapsulated volume or "free (aqueous) phase" represents the space surrounding a liposome. In case of multilamellar liposomes, the terms encapsulated and free phase refer to the interior and exterior volume next to a given membrane from the multilamellar liposome.

"Hold time" refers to the time period for processing the liquid formulations during manufacturing of liposome formulations.

"Size homogeneity" as used herein refers to the size distribution of a particle population. High size homogeneity or narrow size distribution is characterized by a low polydispersity index.

"Lipid" refers to its conventional sense as a generic term encompassing fats, lipids, alcohol-ether-soluble constituents of protoplasm, which are insoluble in water. Lipids usually consist of a hydrophilic and a hydrophobic moiety. In water lipids can self organize to form bilayers membranes, where the hydrophilic moieties (head groups) are oriented towards the aqueous phase, and the lipophilic moieties (acyl chains) are embedded in the bilayers core. Lipids can comprise as well two hydrophilic moieties (bola amphiphiles). In that case, membranes may be formed from a single lipid layer, and not a bilayer. Typical examples for lipids in the current context are fats, fatty oils, essential oils, waxes, steroid, sterols, phospholipids, glycolipids, sulpholipids, aminolipids, chromolipids, and fatty acids. The term encompasses both naturally occurring and synthetic lipids. Preferred lipids in connection with the present invention are: steroids and sterol, particularly cholesterol, phospholipids, including phosphatidyl, phosphatidylcholines and phosphatidylethanolamines, and sphingomyelins. Where there are fatty acids, they could be about 12-24 carbon chains in length, containing up to 6 double bonds. The fatty acids are linked to the backbone, which may be derived from glycerol. The fatty acids within one lipid can be different (asymmetric), or there may be only 1 fatty acid chain present, e.g. lysolecithins. Mixed formulations are also possible, particularly when the non-cationic lipids are derived from natural sources, such as lecithins (phosphatidylcholines) purified from egg yolk, bovine heart, brain, liver or soybean.

"Liposomes" are artificial, self closed vesicular structure of various sizes and structures, where one or several membranes encapsulate an aqueous core. Most typically liposome membranes are formed from lipid bilayers membranes, where the hydrophilic head groups are oriented towards the aqueous environment and the lipid chains are embedded in the lipophilic core. Liposomes can be formed as well from other amphiphilic monomeric and polymeric molecules, such as polymers, like block copolymers, or polypeptides. Unilamellar vesicles are liposomes defined by a single membrane enclosing an aqueous space. In contrast, oligo- or multilamellar vesicles are built up of several membranes. Typically, the membranes are roughly 4 nm thick and are composed of amphiphilic lipids, such as phospholipids, of natural or synthetic origin. Optionally, the membrane properties can be modified by the incorporation of other lipids such as sterols or cholic acid derivatives. Liposomes with particularly flexible membranes based on phospholipids with a low phase transition temperature (i.e. below body temperature) are sometimes referred to as transfersomes.

"Liposomal suspension" refers to a composition comprising liposomes in an aqueous medium.

"Liposomal preparation" or "liposomal composition" refers to any composition comprising liposomes including a liposomal suspension or a dehydrated composition obtained from said suspension by dehydration.

"Lipophilic" refers to the property of a compound to dissolve preferentially in a fat-like (e.g. hydrocarbon) phase, such as a phase being substantially comprised of lipids. The lipophilic property of a compound may be described by the partition coefficient (log P). Compounds of interest in the present context have a log P of greater than about 1, more preferably greater than about 2, most preferably greater than about 3.

"Log P" refers to the partition coefficient of a compound between a water and an octanol phase at 25° C. Generally, a higher log P number means that an agent is better soluble in octanol. The log P is defined as ([concentration of the agent in octanol]/[concentration of the agent in water]). It is well known to the person skilled in the art how the log P of a certain compound can be experimentally determined.

"Low solubility in water" refers to a solubility of a compound which is lower than 0.1 mg/ml, more preferably lower than 0.01 mg/ml and most preferably lower than 0.001 mg/ml in water at physiological pH at 25° C. in the absence of additives that facilitate solubility.

The "overall osmolarity" of a liposomal suspension is the total amount of osmotically active substances present in a certain volume of said suspension divided by the volume of the suspension. For the calculation of the overall osmolarity, osmotically active substances inside and outside the liposomally encapsulated volume of the suspension are likewise considered. In the present context the abbreviations $O_1$ and $O_2$ refer to the overall osmolarity.

"$O_{in}$" and "$O_{out}$" refer to the osmolarity inside and outside a self closed liposome membrane. For unilamellar liposomes $O_{out}$ is the osmolarity of the free aqueous phase, and $O_{in}$ is the osmolarity of the encapsulated volume. For multilamellar liposomes $O_{in}$ and $O_{out}$ refer to the osmolarities inside and outside each individual self closed membrane. In the present context situations where $O_{in}$ is larger than $O_{out}$ are of particular relevance. The relative differences between $O_{in}$ and $O_{out}$ can be investigated by centrifugation techniques, for example by analytical or preparative centrifugation or ultracentrifugation. Because usually an osmotically active compound changes the density of the aqueous phase, differences between $O_{in}$ and $O_{out}$ can be recognized from the sedimentation behavior of the liposomes (Goormaghtigh and Scarborough 1986, Huang and Charlton 1971). In addition, the osmolar gradients can affect structural parameters of the liposome membrane, such as can be determined by methods like X-ray or neutron scattering, or liposome size, such as can be determined by light and X-ray scattering.

An "osmotically active substance" in the present context refers to a substance soluble in water which is not able to substantially permeate the liposome membrane. Typical examples are, for example, ions or sugars, like glucose, or trehalose which can be efficiently entrapped in liposomes, while water molecules display a high permeability and therefore, in the current context, water is not considered an osmotically active substance. The selectivity for permeation of different compounds is a key feature of liposomes (Bangham et al., 1965). Permeability of a compound across a membrane depends on the membrane composition, phase state and other boundary conditions.

"Osmolarity" is the sum of the molar concentrations of solutes present in the aqueous solution, including the biologically active substance and any helper molecules, such as osmotic excipients used to slow the release rate of the active agent. If the solute is present in a dissociated, ionized, or aggregated form, osmolarity is defined as the sum of the molar concentrations of the dissociated, ionized or aggregated forms. The contribution to the osmolarity of a solution made by any solute in the solution is approximately equivalent to the concentration of the solute in the solution divided by its molecular weight. Thus, as a general principle, the larger the molecular weight of a solute, the smaller the osmolarity of the solute, and the smaller the contribution of that solute to the overall osmolarity of the solution. Differences in osmolarity can be determined from changes of various physical chemical parameters; such as density, electron density, refractive index, or viscosity, which can be determined by established methods in physical chemistry.

"Negatively Charged Lipids" refers to lipids that have a negative net charge.

"Pharmaceutical composition" refers to a combination of two or more different components with different pharmaceutical properties than are possessed by either component. In the present invention, the two or more components refer to a lipid or colloidal dispersion and an active agent, optionally together with a pharmaceutically acceptable carrier, diluent and/or adjuvant.

"Physical stability" of a liposome refers to the change of physical state the liposome. A liposome is stable when the physical state is maintained. An important aspect of the physical stability is the release of compound embedded in the liposomal membrane to the aqueous medium of liposomal suspension. The release of compound is a feature of physical instability. The release of compound from the membrane may lead to elevated concentration and aggregation of the compound in the aqueous medium. In the case of taxanes, aggregation is visible by the formation of needles of the taxane. Crystallization of a taxane can be measured by visual inspection of liquid liposomal formulation, light microscopy, light blockage measurement or light scattering. Liposomal size and size distribution or are also features of the physical state of the liposomal suspension.

"Polydispersity" is the width of the distribution of the particle size in a given particle sample, e.g. a liposomal suspension. One measure for the polydispersity is given by the polydispersity index (PI), as obtained from cumulant analysis of photon correlation spectroscopy (PCS) data.

"Polydispersity index" (PI) is a dimensionless number as obtained from so-called cumulant analysis of results from photon correlation spectroscopy (PCS) measurements (Koppel 1972). Cumulant analysis enables model free fitting of PCS data from which the $Z_{average}$, as a measure for the particle size, and the PI value, as a measure for the polydispersity, are obtained. The calculations of these parameters are defined in the ISO standard document 13321:1996 E. In the context of particle size measurements, frequently the terms PCS and Dynamic Light Scattering (DLS), are used synonymously. This technique measures the time-dependent fluctuations in the intensity of scattered light which occur because the particles are undergoing Brownian motion. Analysis of these intensity fluctuations enables the determination of the diffusion coefficients of the particles which are converted into a size distribution. Within the meaning of the present invention, the PI and $Z_{average}$ are determined as disclosed in Example 6.

"Photon correlation spectroscopy" is a technique that measures the time-dependent fluctuations in the intensity of scattered light which occur because the particles are undergoing Brownian motion. Analysis of these intensity fluctuations enables the determination of the diffusion coefficients of the particles which are converted into a size distribution. In the context of particle size measurements, frequently PCS and DLS are used synonymously.

"Positively Charged Lipids" is used as a synonym for cationic lipids (for definition see definition of "cationic lipids"). In the present invention, it is referred to environments where the pH is in the range between 3 and 9, preferably between 5 and 8.

"Stability" may refer to physical stability of a liposome and to the chemical stability of the single constituents (e.g. lipids and active compound) comprised in the liposome.

"Stressed liposomes" or "stressed liposomal preparations" refers to liposomes wherein the liposome membrane is under tensile stress and to preparations comprising such liposomes.

"Tensile stress" on the liposome membrane in the current context can be exerted by application of a concentration gradient of an osmotically active compound between the aqueous phase inside and outside a liposomally encapsulated volume. If the inside osmolarity $O_{in}$, is higher than the outside osmolarity $O_{out}$, this will result in an increase of the pressure gradient, $\Delta P$, between the encapsulated and the free volume by osmotic forces. The excess pressure is balanced by the surface tension, $\gamma$, at the liposome membrane, where the correlation between the pressure gradient and the surface tension is given by the well known Young-Laplace equation (Evans and Wennerström, 1994).

$$\gamma = \frac{\Delta P \cdot r}{2} \quad \text{(Formula 1)}$$

For the present liposome systems it has to be taken into account that the exerted surface tension leads to an area expansion of the liposome membrane which may result in changes of the radius, encapsulated volume, and, consequently, to changes of the osmolarity of that encapsulated volume. The area expansion, $\Delta A$, as a function of the surface tension depends on the elastic modulus of the membrane, $\kappa$, and is given by the Young equation as:

$$\frac{\Delta A}{A} = \frac{\gamma}{\kappa} \quad \text{(Formula 2)}$$

Formula 1 makes clear, that the relation between surface tension and pressure is radius dependent. At a given pressure gradient, the surface tension increases with increasing radius. The area increase and the corresponding size increase of the liposomes is larger for big liposomes than for smaller ones. For systems with given surface tension, such as soap bubbles, the pressure gradient $p_{inside}-p_{outside}$ increases with decreasing radius, or, in other words, with increasing curvature.

"Therapeutically active agent" or "therapeutic agent" refers to an agent which prevents or reduces the extent a pathologic condition in an animal, particularly in a mammal, preferably in humans.

"Small molecule" refers to a molecule with a molecular weight of less than about 2000 Da.

"Zeta potential" refers to measured electrostatic potential of a colloidal particle in aqueous environment, measured with an instrument such as a Zetasizer 3000 using Laser Doppler micro-electrophoresis in about 0.05 mM KCl solution at about pH 7.5. The zeta potential describes the potential at the boundary between bulk solution and the region of hydrodynamic shear or diffuse layer. The term is synonymous with "electrokinetic potential" because it is the potential of the particles which acts outwardly and is responsible for the particle's electrokinetic behaviour.

DETAILED DESCRIPTION

An inventive process for the manufacture of a liposomal preparation can be performed by the following steps:

a) providing a first liposomal preparation comprising a suspension of liposomes in an aqueous phase, wherein the liposomes comprise at least one membrane, wherein the membrane encloses a liposomally encapsulated volume of the aqueous phase and the aqueous phase comprises at least one osmotically active substance and has an initial overall osmolarity, $O_1$, thereafter b) generating an osmolar gradient in the aqueous phase of said preparation wherein the osmolarity of the aqueous phase outside the liposomally encapsulated volume, $O_{out}$, is lower than the osmolarity of the aqueous phase inside the liposomally encapsulated volume, $O_{in}$, to yield a second (stressed) liposomal preparation, c) optionally dehydrating the second (stressed) liposomal preparation to obtain a dehydrated preparation, and d) optionally rehydrating the dehydrated preparation.

The liposomal preparation of step a) preferably comprises at least one lipophilic agent present in the liposomal membrane. The lipophilic agents, however, may also be added at later stages of the production process.

Step b) can be performed by reducing the initial overall osmolarity, $O_1$, of the liposomal preparation derived from step a) to yield a stressed liposomal preparation with the overall osmolarity, $O_2$, which is lower than the osmolarity $O_1$.

Within the context of the present invention, reducing the overall osmolarity $O_1$ relates to a process wherein initially the osmolarity of the aqueous medium outside the liposomally encapsulated volume, $O_{out}$, is reduced. If one assumes initially an identical concentration in all compartments, $O_1=O_{out}=O_{in}$, dilution affects first of all only the free aqueous phase, $O_{out}$, resulting in $O_{out}<O_{in}$. Consequently an osmotic gradient between the inside and the outside of the liposomally encapsulated volume is generated. It is well understood, that in presence of an osmotic gradient, liposomes may swell, because the membranes are permeable for water molecules. Therefore, as a secondary effect of dilution, also the osmolarity of the encapsulated aqueous medium, $O_2$, may decrease to certain extend. The absolute changes of osmolarity depend on various factors like, fraction of encapsulated volume, liposome size, membrane elasticity (Young's modulus) etc. Thus the ratio between $O_1$ and $O_2$, is not necessarily identical to the ration between $O_{in}$ and $O_{out}$ after dilution.

However, reduction of the osmolarity in the free, non encapsulated aqueous phase will lead to an increase of the osmolarity gradient $O_{in}$-$O_{out}$ between the exterior and the interior of the encapsulated phase. If swelling in response to osmotic stress occurs beyond a certain factor, membrane defects may be formed, allowing the release of solute from the phase of higher osmolarity to the phase of lower osmolarity. This will reduce the osmolar gradient and the osmolar stress. The membranes may reseal under conditions of maximum tensile stress and maximum critical limit of osmotic gradient for pore formation. Therefore the system can be considered self stabilizing, in the sense, that if an excess gradient is applied, irrespective of detailed conditions, the system will adopt the state of maximum osmotic gradient. Such an effect may be considered favourable for assurance of reproducible conditions during manufacturing.

The liposomes used within the context of the present invention may comprise neutral, anionic and/or cationic lipids. Neutral or anionic lipids may be selected from sterols or lipids such as cholesterol, phospholipids, lysolipids, lysophospholipids, sphingolipids or pegylated lipids with a neutral or negative net charge. Useful neutral and anionic lipids thereby include: phosphatidylserine, phosphatidylglycerol, phosphatidylinositol (not limited to a specific sugar), fatty acids, sterols, containing a carboxylic acid group for example, cholesterol, 1,2-diacyl-sn-glycero-3-phosphoethanolamine, including, but not limited to, 1,2-dioleylphosphoethanolamine (DOPE), 1,2-dihexadecyl-phosphoethanolamine (DHPE), 1,2-diacyl-glycero-3-phosphocholines, 1,2-distearylphosphosphatidylcholine (DSPC), 1,2-dipalmitylphosphosphatidylcholine (DPPC), 1,2-dimyristylphosphosphatidylcholine (DMPC), phosphatidylcholine preferably egg PC, soy PC and sphingomyelin. The fatty acids linked to the glycerol backbone are not limited to a specific length or number of double bonds. Phospholipids may also have two different fatty acids. Preferably the further lipids are in the liquid crystalline state at room temperature and they are miscible (i.e. a uniform phase can be formed and no phase separation or domain formation occurs) with the used cationic lipid, in the ratio as they are applied. In a preferred embodiment the neutral lipid is 1,2-dioleylphosphosphatidylcholine (DOPC).

The preferred cationic lipids of the liposomal preparation are N-[1-(2,3-dioleoyloxy)propyl]-N,N,N-trimethyl ammonium salts, e.g. the methylsulfate salt. Preferred representatives of the family of -TAP (trimethylammonium methylsulfate) lipids are DOTAP (dioleoyl-), DOTAP (dimyristoyl-), DPTAP (dipalmitoyl-), or DSTAP (distearoyl-). Other useful lipids for the present invention may include: DDAB, dimethyldioctadecyl ammonium bromide; 1,2-diacyloxy-3-trimethylammonium propanes, (including but not limited to: dioleoyl, dimyristoyl, dilauroyl, dipalmitoyl and distearoyl; also two different acyl chains can be linked to the glycerol backbone); N-[1-(2,3-dioloyloxy)propyl]-N,N-dimethyl amine (DODAP); 1,2-diacyloxy-3-dimethylammonium propanes, (including but not limited to: dioleoyl, dimyristoyl, dilauroyl, dipalmitoyl and distearoyl; also two different acyl chain can be linked to the glycerol backbone); N-[1-(2,3-dioleyloxy)propyl]-N,N,N-trimethylammonium chloride (DOTMA); 1,2-dialkyloxy-3-dimethylammonium propanes, (including but not limited to: dioleyl, dimyristyl, dilauryl, dipalmityl and distearyl; also two different alkyl chain can be linked to the glycerol backbone); dioctadecylamidoglycylspermine (DOGS); 3β-[N—(N',N'-dimethylamino-ethane)carbamoyl]cholesterol (DC-Chol); 2,3-dioleoyloxy-N-(2-(sperminecarboxamido)-ethyl)-N,N-dimethyl-1-propanaminium trifluoro-acetate (DOSPA); β-alanyl cholesterol; cetyl trimethyl ammonium bromide (CTAB); diC14-amidine; N-tert-butyl-N'-tetradecyl-3-tetradecylamino-propionamidine; 14Dea2; N-(alpha-trimethylammonioacetyl)didodecyl-D-glutamate chloride (TMAG); O,O'-ditetradecanoyl-N-(trimethylammonio-acetyl)diethanolamine chloride; 1,3-dioleoyloxy-2-(6-carboxy-spermyl)-propylamide (DOSPER); N,N,N',N'-tetramethyl-N,N'-bis(2-hydroxylethyl)-2,3-dioleoyloxy-1,4-butanediammonium iodide; 1-[2-(acyloxy)ethyl]2-alkyl(alkenyl)-3-(2-hydroxyethyl)-imidazolinium chloride derivatives as described by Solodin et al. (Solodin et al., 1995), such as 1-[2-(9(Z)-octadecenoyloxy)ethyl]-2-(8(Z)-heptadecenyl-3-(2-hydroxyethyl)imidazolinium chloride (DOTIM), 1-[2-(hexadecanoyloxy)ethyl]-2-pentadecyl-3-(2-hydroxyethyl) imidazolinium chloride (DPTIM), 2,3-dialkyloxypropyl quaternary ammonium compound derivatives, containing a hydroxyalkyl moiety on the quaternary amine, as described e.g. by Feigner et al. (Feigner et al., 1994) such as: 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimetyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), 1,2-disteryloxypropyl-3-dimethyl-hydroxyethyl ammonium bromide (DSRIE); cationic esters of acyl carnitines as reported by Santaniello et al. (U.S. Pat. No. 5,498,633); cationic triesters of phosphatidylcholine, i.e. 1,2-diacyl-sn-glycerol-3-ethylphosphocholines, where the hydrocarbon chains can be saturated or unsaturated and branched or non-branched with a chain length from $C_{12}$ to $C_{24}$, the two acyl chains being not necessarily identical.

The liposomes may have different sizes, lamellarity and structure. Preferably the liposomes have an average diameter $Z_{average}$ of about 50 nm to about 500 nm. Most preferred is a size $Z_{average}$ of about 100 to about 200 nm. The liposomes may be uni-, oligo- or multilamellar liposomes. Preferably the liposomes are unilamellar liposomes.

The active agent or cosmetic agent employed in the different embodiments of the invention compound preferably has a log P of greater than 1, more preferably greater than about 2, most preferably greater than about 3.

The active agent or cosmetic agent employed in the different embodiments of the invention preferably has a low solubility in water. Preferably the compound has a solubility of lower than 0.1 mg/ml, more preferably lower than 0.01 mg/ml and most preferably lower than 0.001 mg/ml in water at physiological pH at ambient temperature.

Preferably the active agent comprised in the liposomes of the present invention is a therapeutically or diagnostically active agent. Most preferably the compound is therapeutically active.

Preferably the active agent or cosmetic agent is a molecule with a molecular weight less than 2000 Da, more preferably less that 1000 Da.

In one aspect, the active agent may be selected from the group comprising abarelix, altretamine, anastrozole, aprepitant, bicalutamide, camptothecins, capecitabine, chlorotrianisene, conjugated estrogens, cyclosporine, dactinomycin, diethylstilbestrol, docetaxel, dolasetron, dromostanolone, epirubicin, epothilones, e.g. epothilone B, epothilone D, or epothilone derivatives, e.g. as disclosed in WO2004048372, WO2004007492, WO2005051947 and WO2005030767 (the content of which is herein incorporated by reference), suberlotinib, ethinyl estradiol, exemestane, fentanyl, flavopiridol, fluoxymesterone, fulvestrant, gefitinib, granisetron, hesperetin, hydromorphone, irinotecan, ketoconazole lapatinib, letrozole, leuprolide, lomustine, lucanthone, marinol, masoprocol, megestrol, nabilone, nilutamide, palonosetron, porfimer, quinestrol, quinestrol, tamoxifen, taxanes, temsirolimus, testolactone, topotecan, toremifene, trimetrexate, valrubicin, vinblastine, vitamin E, and derivatives of these compounds. Preferably the compound is a taxane, most preferably paclitaxel or a derivative thereof.

In a certain aspect of the invention, the active agent is not a nucleotide or polynucleotide molecule like a DNA or RNA molecule.

In another aspect the scope of the invention does not comprise active agents which are ionized during formulation and/or active agents which are highly water soluble compounds as for example adriamycin.

Preferably, the liposomes of the invention comprise between about 2.5 mol % and about 4.5 mol % of paclitaxel in the liposomal membranes. Thus, paclitaxel may preferably represent an amount of between about 2.5 mol % and about 4.5 mol % of the amount of all molecules present in the membranes such as lipids and related molecules and paclitaxel. More preferably, these liposomes show an impeded drug release as a suspension and/or after rehydration, and/or do not substantially form crystals during storage as defined herein below.

In a specially preferred embodiment of the invention, the liposomes are cationic liposomes, e.g. cationic liposomes comprising DOTAP, DOPC and paclitaxel in a molar ratio of about 50:47:3. Formulations of this composition are known in the art as MBT-0206 or EndoTAG-1. The manufacture of liposomal preparations comprising DOTAP, DOPC and paclitaxel is disclosed in WO 2004/002468, the content of which is herein incorporated by reference.

In general liposomes may be prepared by methods which are well known to the person skilled in the art. Various methods to prepare liposomes are disclosed by New et al. (1990).

Preferably the liposomes employed in the present invention are prepared by ethanol injection.

In a special embodiment of the invention, the liposomes have a positive zeta potential, more preferably a zeta potential of greater than about +30 mV.

The osmotically active substance employed in the inventive method or comprised in the inventive compositions is soluble substance which is not able to substantially permeate a lipid bilayer. Preferably the osmotically active substance is present inside and outside of the liposomes.

The osmotically active substance may be an organic molecule like a saccharide, e.g. a mono-, di-, oligo- or poly saccharide, a sugar alcohol, an amino acid, a peptide, a protein, a water-soluble polymer, an organic- or inorganic salt, ion, or a combination thereof.

Useful saccharides include sugar and sugar alcohols, oligosaccharides, water soluble polysaccharides and derivatives thereof. Preferred saccharides according to the invention include glucose, fructose, lactose, sucrose, maltose, cellobiose, galactose, maltotriose, maltopentose, raffinose, dextrin, dextran, inulin, mannitol, sorbitol, xylitol, chitosan and most preferably trehalose.

Examples of water soluble polymers are polyethylene glycols, polyvinylalcohol, polyacrylates, or polyvinylpyrrolidone.

In a certain aspect, the use of an osmotically active substance in the inventive method or compositions excludes the use of complexing agents that facilitate the solubilisation of compounds that have a low solubility in water. Examples of such complexing agents are cyclodextrins as disclosed by Zhang et al. in WO 2007/005754 or MacLachlan et al. in WO 2007/012191.

The aqueous medium or phase used within the context of the present invention may comprise one or more further constituents which are at least partially miscible with water, such as alcohols (e.g. $C_{1-4}$ alcohols such as ethanol) or ketones (e.g. $C_{1-4}$ ketones such as acetone). In a preferred embodiment of the invention, the aqueous phase contains ethanol.

The aqueous phase may further comprise a buffer substance or other stabilizing agents. Suitable buffer substances are selected from e.g. acetic acid, Tris, Bis, phosphoric acid, lactic acid and the like, preferably citric acid. The buffer substance may established a pH of the aqueous medium between about 3 and 7, preferably between about 4 and about 5.

Preferably, the liposomal preparation of step a) is manufactured by mixing an organic solution (e.g. ethanol) comprising lipids and optionally an active agent or cosmetic agent into an aqueous medium comprising at least one osmotically active substance characterized by an overall osmolarity $O_1$.

The preferred range of osmotic gradients, $O_{in}$-$O_{out}$, is between 10 mOsm and 2000 mOsm, more specifically between 50 mOsm and 1000 mOsm and even more specifically between 100 mOsm and 1000 mOsm.

The osmotic gradients may also be indicated by the concentration difference between the concentration of the osmotically active substance inside the liposomally encapsulated volume and the concentration of the osmotically active substance outside the liposomally encapsulated volume. The preferred range of osmotic gradients is a concentration difference between 5% and 30% by weight (w/w), i.e. a gradient between 0% of the osmotically active substance outside the encapsulated volume and between 5% and 30% by weight of the substance inside the encapsulated volume, or 10% of the osmotically active substance outside the encapsulated volume and between 15% and 40% by weight of the substance inside the encapsulated volume.

The liposomal preparation derived from step a) may be subjected to a homogenisation step, which may be performed by extrusion, filtration through membrane filters, high pressure homogenisation and/or high speed homogenization and mostly preferred by extrusion through a membrane, e.g. with a pore size of about 200 nm under pressure. Membranes with other pore sizes such as 50 nm, 100 nm, 150 nm, 400 nm well known in the art may be used as well. Filtration through membrane filters maybe performed by filtration through membranes composed of PVDF, PES, nylon-filters but also other materials may be used if defined to be suitable. The pore size of membranes is preferably in the range of about 200 nm to 450 nm, but pore size is not limited to the sizes mentioned. Different materials and different pore sizes may be combined in a way to obtain a solution which maybe processed by a sterilizing grade filtration. In a preferred embodiment, the liposomes derived from step a) are subjected to homogenisation before an osmolar gradient is generated.

Since sterility is a mandatory feature for pharmaceutical products, the liposomal suspensions employed in the inventive process may be sterilised at some stage during the process. Preferably the suspensions are sterilised by filtering through a sterilising grade sterile filtration membrane (0.22 pm). In a preferred embodiment, liposomal suspensions are sterilized by filtering after an osmolar gradient is generated according to step b) of the invention.

According to the general concept of the invention the osmotic gradient between the encapsulated and the free volume may be generated or altered once or several times at different stages during the production process of a liposomal preparation. This can possibly be achieved by the same or different procedures as described in the following.

In a preferred embodiment of the invention, step b) of the inventive process may comprise the steps of b1) dehydrating the liposomal preparation derived from step a) to obtain a dehydrated liposomal preparation, and b2) rehydrating said dehydrated liposomal preparation, preferably in an aqueous medium under conditions, wherein a stressed liposomal preparation is obtained.

Within the meaning of the present invention "liposomal preparation derived from step a)" relates to a liposomal preparation prepared in step a) or any liposomal preparation which can be obtained from the liposomal preparation prepared in step a) via different processing steps. These processing steps may for example include homogenisation and/or sterilisation as described above.

In a preferred embodiment, the generation or alteration of an osmolar gradient is performed at least once after the manufacture of the first liposomal preparation in step a) and before the dehydration of said liposomal preparation derived from step a). Preferably generation or alteration of the osmolar gradient is performed after an extrusion step and/or after sterile filtration. As mentioned above, the osmolar gradient enhances the stability of the liposomal suspension subjected to the processing steps.

Preferably the dehydration is performed at temperatures above room temperature.

In an especially preferred embodiment of the invention, the dehydration of step b1) is performed by spay-drying the liposomal suspension. In the spray-drying process, the liposomal suspension is first atomised into small droplets by spraying said suspension. Subsequently the liposomes are dried by the evaporation of the medium from the droplets at elevated temperatures. The drying of the liposomes after droplet formation may be achieved by contacting the droplets with a provided, dry, possibly heated, gas stream to obtain solid particles. The possible gaseous stream may be an inert gas or air. The drying gas can preferably be a low-oxygen gas containing less than 0.1 vol. %, preferably less than 0.05 vol. %, oxygen or an oxygen-free gas. Inert gaseous are increasing the safety of a heated drying systems that contains highly flammable solutions, by pumping nitrogen, carbon dioxide, helium, neon, argon, krypton, xenon and radon or some other inert gas in order to displace oxygen. The effect of these systems is to either completely remove the oxygen, or reduce it to a negligible level. In a preferred embodiment nitrogen is used as an inert gaseous. In another embodiment of the invention the inert gas protects the active ingredients and excipients containing in the formulation. Preferably the spray-drying is performed in a suitable device for spray drying. The dehydrated liposomes are separated from the gas stream and collected. The spray drying can be performed under excess pressure, normal pressure or partial vacuum. A favourable process pressure range can exist if powder conforming to specification is produced with the drying gas at the maximum permissible system temperature and at maximum capacity. For the selection of drying conditions, the combination of parameters like liquid feed rate, drying gas rate, drying gas temperature, thermodynamic parameters of the excipients, and stability limits of the compounds has to be taken into account. Important parameters are the inlet temperature of the drying gas $T_{in}$, and the outlet temperature, $T_{out}$, which is present inside the spray dryer. $T_{out}$ is substantially lower that $T_{in}$ due adiabatic cooling on evaporation. The actual temperature of the particle surface can be significantly lower that $T_{out}$, depending on the local evaporation rate. Therefore no generic spray drying parameters can be defined. For drying liposomes, the temperature inside the process chamber may range between 10° C. and 200° C. More typically, the suspension are dried by the method of the invention with 30° C. to 150° C., and more preferably from about 60° C. to about 120° C.

Equipment for the spray-drying process may be obtained from Büchi (Flawil, Switzerland), or GEA Niro (Soeborg, Denmark) or custom made. The person skilled in the art is able to select the conditions of the drying process, for example feed rates and temperatures, depending on the suspension to be dried, the equipment used and the desired specifications.

Especially, the conditions of the dehydration step may be chosen to obtain a dehydrated liposomal composition with a very low amount of organic solvent. The dehydration by spray-drying is especially suitable for obtaining low amounts of residual organic solvent.

Also the dehydration by spray-drying as described herein results in a dehydrated liposome composition in form of a pourable powder. Such powders have improved handling properties, for example with regard to the filling of such dehydrated compositions, as compared to dehydrated compositions obtained by freeze-drying which have a cake-like structure.

In one aspect of the invention, dehydration does not substantially affect the ratio between encapsulated and free osmotically active compound when comparing the ratio in the liposomal suspension that has been subjected to spray drying and the ratio in the spray-dyed preparation after rehydration in water.

In a certain aspect of the invention the dehydration by lyophilisation, or freeze drying, wherein a liposomal suspension is frozen and subsequently subjected to reduced pressure to withdraw water molecules is not included within the scope of the invention.

The dehydrated composition, e.g. as obtained in step b1) or c) may be filled into suitable containers and may be stored for a certain period of time. Preferably the composition is filled and stored under sterile conditions. Storage time may be from several days to several month or even years. The composition may be stored at room temperature, at temperatures between 2° C. to 8° C. or below 0° C.

Before the dehydrated liposomal composition is used, for example administered to a patient in case of a liposomal composition used as a pharmaceutical composition, or further processed, the dehydrated composition is rehydrated according to step b2 or c). For this purpose the dehydrated composition obtained as described above is mixed with an aqueous medium. To enhance rehydration, the mixture may be stirred or swirled.

The osmolarity of the aqueous medium used for rehydration is lower than the overall osmolarity $O_1$ of the suspension that had been subjected to the dehydration step. Preferably the aqueous medium used for rehydration does not substantially comprise osmotically active substances. Most preferably, pharmaceutical grade water for injection is used for rehydration.

In some embodiments, the volume of aqueous medium used for rehydration may be larger than the volume of liposomal suspension which has been dehydrated to obtain the respective amount of dehydrated liposomal composition.

According to the invention the, osmolarity of the aqueous medium used for rehydration and the volume of the medium used for rehydration are selected in a combination to obtain a rehydrated suspension which has an overall osmolarity $O_2$ which is lower than the osmolarity $O_1$ of the suspension which has been subjected to the dehydration step.

In another aspect of the invention, step b) is performed by diluting the liposomal suspension derived from step a) to yield an aqueous medium having an overall osmolarity $O_2$ which is lower than $O_1$.

The liposomal suspension is diluted with an aqueous medium as described above. In a preferred embodiment, the liposomal suspension is diluted with water. In one embodiment, the aqueous medium used to dilute the liposomal suspension does not comprise an active agent, especially not an active agent which is to be encapsulated into the liposomes.

In a preferred embodiment of the invention $O_2$ is at least 10 mOsm lower than $O_1$, more preferably $O_2$ is at least 50 mOsm lower than $O_1$, and even more preferably $O_2$ is at least 100 mOsm lower than $O_1$.

In another aspect of the invention, step b) is performed by dialysing the liposomal suspension derived from step a) against an aqueous medium having an overall osmolarity which is lower than Preferably dialysis is performed under conditions to yield an osmotic gradient between $O_1$ and the osmolarity of the aqueous medium against which the dialysis is performed of at least 10 mOsm more preferably at least 50 mOsm and even more preferably at least 100 mOsm.

Alternatively step b) may be performed by other suitable methods. For example the concentration of the osmotically active substance may be reduced by suitable chromatographically methods such as ion exchange or affinity chromatography.

In a further aspect of the invention, the stressed liposomal suspension obtained according to step b) the process described as above may be dehydrated. Dehydration of said stressed liposomal suspension may be performed by any suitable process known to the person skilled in the art. Suitable drying procedures are for example freeze-drying, spray-freeze-drying or spray-drying. In preferred embodiment dehydration by spray drying may be performed as described above for step b1). In a further aspect of the invention, the resulting dehydrated liposomal preparation is rehydrated as described above.

In a specific embodiment the invention relates to a process wherein an initial liposomal suspension, preferably comprising cationic liposomes comprising DOTAP and optionally DOPC as lipids, and further comprising a lipophilic active agent, preferably paclitaxel, in the liposomal membrane, are prepared in an aqueous trehalose phase. The concentration of the constituents of the liposomal suspension are present in an about three fold concentration as compared to the liposomal suspension yielded by the process which is finally used, e.g. administered to a human. Preferably the initial liposomal suspension has a concentration of about 30 mM lipids and about 30 mg/ml, more preferably 29.4 mg/ml trehalose. The initial liposomal suspension is optionally homogenized by extrusion through a membrane in the next step. Subsequently the overall osmolarity of the liposomal suspension is reduced, preferably by a factor of 1.5, preferably by diluting the volume of the liposomal suspension with water e.g. to the 1.5 fold volume. Subsequently the liposomal suspension is optionally sterilized, preferably by filtration. In the next step the liposomal suspension is dehydrated, preferably by spray drying, to yield a dehydrated liposomal suspension. The dehydrated liposomal suspension is finally rehydrated to yield a liposomal suspension, which is used for its respective purpose, such as administration to a human. The latter liposomal suspension preferably has a concentration of about 10 mM lipids and about 10 mg/ml, preferably 9.79 mg/ml trehalose.

In another aspect the invention relates to a process for manufacturing a liposomal preparation, comprising:

i) providing a liposomal suspension, wherein at least one osmotically active substance is comprised in the aqueous phase of the suspension, wherein a higher osmolarity is present inside the liposomally encapsulated volume than outside the liposomally encapsulated volume, ii) incubating said liposomal suspension with a lipophilic compound, optionally in an unsolubilized form, iii) optionally separating any unsolubilized compound from the liposomal suspension, e.g. by filtration, centrifugation or other suitable methods, iv) optionally dehydrating the liposomal preparation, and v) optionally rehydrating the dehydrated liposomal preparation.

Preferably the osmotic gradient between the inside and the outside of the liposomally encapsulated volume is between 10 mOsm and 2000 mOsm, more specifically between 50 mOsm and 1000 mOsm and even more specifically between 100 mOsm and 1000 mOsm.

In a preferred embodiment of the invention the liposomal suspension of step i) does not comprise an active agent or cosmetic agent.

The liposomes comprising an osmotic gradient of step i) can be prepared as described above. In a preferred embodiment of the invention, there is no active or cosmetic agent added in the manufacture of the liposomal suspension of step i). The unsolubilised form of the active agent or cosmetic agent may be for example a crystalline form, e.g. of different morphology and size or a powder form.

In one embodiment of the invention, unsolubilised agent is separated from the dispersion after the incubation. In a preferred embodiment, undissolved compound is separated by centrifugation or filtration. Filtration might be performed in a syringe filter.

In another aspect the invention relates to a liposomal preparation obtained or obtainable by the processes as described above. The preparation might be in dehydrated form or in form of an aqueous suspension.

The liposomal preparation of the present invention is preferably used in medicine, e.g. in human or veterinary medicine. The preparation is preferably administered intravenously. More preferably the preparation is used for the treatment of cancer such as bladder cancer, breast cancer, colorectal cancer, endometrial cancer, leukaemia, lung cancer, lymphoma, melanoma, non-small-cell lung cancer, ovarian cancer, prostate cancer and to childhood cancers such as brain stem glioma, cerebellar astrocytoma, cerebral astrocytoma, ependymoma, Ewing's sarcoma/family of tumors, germ cell tumor, extracranial, Hodgkin's disease, leukaemia, acute lymphoblastic, leukaemia, acute myeloid, liver cancer, medulloblastoma, neuroblastoma, non-Hodgkin's lymphoma, osteosarcoma/malignant fibrous histiocytoma of bone, retinoblastoma, rhabdomyosarcoma, soft tissue sarcoma, supratentorial primitive neuroectodermal and pineal tumors, unusual childhood cancers, visual pathway and hypothalamic glioma, Wilms tumor and other childhood kidney tumors and to less common cancers including acute lymphocytic leukaemia, adult acute myeloid leukaemia, adult non-Hodgkin's lymphoma, brain tumor, cervical cancer, childhood cancers, childhood sarcoma, chronic lymphocytic leukaemia, chronic myeloid leukaemia, esophageal cancer, hairy cell leukaemia, kidney cancer, liver cancer, multiple myeloma, neuroblastoma, oral cancer, pancreatic cancer, primary central nervous system lymphoma, skin cancer, small-cell lung cancer, head & neck cancer, gall bladder and bile duct cancer, stomach cancer, gastrointestinal cancer, Kaposi's sarcoma, urothelial cell carcinoma, thyroid gland carcinoma, testicular carcinoma, vaginal cancer, angiosarcoma, soft tissue sarcoma, mesothelioma and hepatocellular carcinoma. Particularly, the cancer may be a mestastasing cancer and/or a standard (chemo) therapy-resistant cancer. Administration of the composition of the invention may slow or stop disease progression, or may lead to a partial or complete remission in a human. Most preferably pancreatic or breast cancer, especially triple receptor negative breast cancer is treated. The liposomal preparation of the present invention can be administered at a unit dose of about 11 mg/m² paclitaxel to about 44 mg/m² paclitaxel, preferably at a unit dose of about 22 mg/m² paclitaxel. Preferably the preparations are administered once or twice weekly. The liposomal preparations can be used as disclosed in WO2005/039533, WO 2006/117220, and WO 2007/107305.

Furthermore the liposomal preparation of the present invention may be used as a diagnostic or cosmetic preparation.

Furthermore the invention relates to a liposomal suspension comprising an active or cosmetic compound in the liposomal membranes, wherein the liposomes encapsulate an aqueous medium of an osmolarity which is higher than the osmolarity of the aqueous medium outside of the liposomally encapsulated volume. The aqueous medium of the suspension comprises at least one osmotically active substance. The difference between osmolarity of the medium inside of the liposome and outside of the liposome is preferably at least 10 mOsm, preferably at least 50 mOsm.

The difference of osmolarity inside and outside the liposome induces an osmotic pressure gradient which leads to tensile stress on the liposome membrane, such as described in Hallet et al., 1993. Accordingly the invention relates to a liposomal suspension comprising an active or cosmetic compound in the liposomal membrane, wherein the liposomal membrane is under tensile stress.

Liposomes wherein the liposomal membrane is under tensile stress can be obtained by application of osmotic gradients as described above.

Several methods of physico-chemical characterization can be applied to determine osmolar gradients and tensile stress in liposome preparations. In many cases, solutions of osmotically active components have a density higher than that of water and the density changes monotonously with the concentration of the compound. If the osmolarity of the liposome encapsulated volume is higher than that of the free volume, this affects the liposome density. For trehalose at a concentration of 5% (150 mOsm) in water the density is about 0.02 g/l higher that that of pure water (Handbook of Chemistry and Physics, CRC Press, Boca Raton, Fla.). Consequently, the difference of osmolarity inside and outside the liposome leads to a different density of the medium inside the liposomally encapsulated volume and the medium outside the liposomally encapsulated volume.

Thus it is a further aspect of the invention to disclose liposomal suspensions, wherein the liposomally encapsulated volume has a higher density than the medium outside the liposomally encapsulated volume. The difference in density is given by the preferred osmolar gradient and the density of the solution of the respective osmotically active compound. The density of colloidal particles, such as liposomes, may be determined for example by ultracentrifugation methods.

A specifically preferred embodiment of the inventive liposomal suspensions comprising an osmolar gradient is a liposomal suspension comprising liposomes comprising DOTAP, DOPC, and paclitaxel, preferably in a molar ration of 50:47:3, at a total lipid concentration of about 10 mM, trehalose, and optionally citric acid, suspended in an aqueous phase comprising about 10 mg/ml, especially 9.79 mg/ml trehalose, and optionally about 0.011 mg/ml citric acid, wherein said liposomes have an anhydrous density of at least about 1.1 g/ml, especially at least about 1.15 g/ml, at least about 1.17 g/ml, or at least about 1.17 g/ml. Preferably the said liposomes have a $z_{average}$ of about 140 nm.

The above described process enables the preparation of liposomal suspensions comprising liposomes as described above which are furthermore characterised by a controlled particle size distribution, where the width of the size distribution profile is not substantially broadened by the manufacturing process, as characterised for example, by changes of the polidispersity index (PI). Preferably the PI of the inventive liposomal suspension comprising an osmolar gradient is not elevated by more than 0.2, more preferably it is not elevated by more that 0.1, by the generation of the osmolar gradient.

In a further aspect of the invention the active or cosmetic compound is substantially only comprised in the membrane compartment of the liposomes in the inventive liposomal preparations. Thus, at least about 98%, preferably at least about 99% of the molar amount of all active or cosmetic compound present in the preparation is embedded in the lipidic phase of the liposomal membranes. Only the remaining amount may be solubilised in the aqueous phase of the preparation or may be present in form of crystallised active or cosmetic compound.

The suspensions disclosed herein which can be obtained by the disclosed process are more stable with respect to drug release than comparable conventional liposomal suspensions which are prepared without an osmotic gradient. The temporal stability with respect to drug release from the liposomes is higher, and the formulation is less prone to drug release when subjected to mechanical stress and/or other stress. Preferably, drug release can be impeded at least for 6 hours, preferably at least for 12 hours, at least for 24 hours, at least for 2 d, at least for 7 d or at least for 14 d or more at 25° C., compared to a suspension without an osmotic gradient. Determination of drug release depends on the type of drug. For paclitaxel loaded liposomes, drug release can be sensitively monitored by determining drug particles (crystals) which form after release. Particles can be determined, for example by X-ray diffraction measurements, or light scattering techniques.

In one embodiment of the invention, at least about 90%, preferably at least about 95%, most preferably 99% of the amount of active or cosmetic compound solubilised by the liposomal membranes is maintained in the liposomes over at least about 24 hours at room temperature and not released into the aqueous phase of the suspensions. Since the release of lipophilic active or cosmetic compounds, which have a low solubility in said aqueous phase, may lead to crystal formation, the inventive suspensions do not substantially form crystals to an amount corresponding to more than about 10%, preferably more than about 5%, most preferably more than about 1% of the solubilised material in 24 hours at 25° C.

Also the inventive liposomal suspensions obtained by rehydration of a dehydrated liposomal composition as described above do not form aggregates over a period of at least about 24 hours at 25° C. Formation of aggregates may be determined by measuring changes in the $Z_{average}$ and PI via photon correlation spectroscopy (PCS). The inventive suspensions are characterized by changes of the $Z_{average}$ by not more than a factor of about 1.5, preferably not more than 1.25, and changes of the PI value by not more that a factor of about 2, preferably not more than about 1.5, most preferably not more than about 1.25 over 24 hours. Preferably the liposomal suspensions with these properties are derived from rehydration of a dehydrated liposomal composition.

Since organic solvents are frequently used in the preparation of liposomes, e.g. as described above for the ethanol injection method, residual organic solvent, such as ethanol, is usually found in the dehydrated liposomal product, and accordingly in the rehydrated liposomal suspension derived from it. This is especially the case for liposomal preparations which have been dehydrated by freeze-drying (lyophilisation). However it is desirable for liposomal product used for application to humans to comprise as little organic solvent as possible. The present invention enables dehydration by spray-drying, which facilitates the removal of most or all residual organic solvent, while obtaining liposomes with a high stability. Accordingly it is another aspect of the invention to disclose dehydrated liposomal preparations as described above which comprise about less than 1% w/w, more preferably about less than 0.5% w/w, most preferably about less than 0.1% w/w of organic solvent based on the total weight of the dehydrated preparation. By rehydration of these dehydrated liposomal preparations, liposomal suspensions are obtained, which comprise about less than 1 mg/mL, more preferably about less than 0.5 mg/mL, most preferably about less than 0.1 mg/mL organic solvent. Preferably the organic solvent is ethanol.

Furthermore the inventive liposomal suspensions, which are obtained by rehydration of a dehydrated liposomal composition as described above, have a very similar size distribution profile compared to the original liposomal suspensions that were dehydrated as described above. More specifically, the liposome size is well maintained and no significant formation of lipid aggregates as determined from PCS measurement is encountered. In one embodiment of the invention, the liposomal suspension subjected to dehydration and the liposomal suspension obtained by rehydration as described above are characterised by a $Z_{average}$ which differs by less than a factor of 1.5 and a PI value which differs by less than a factor of two (from PCS measurements). The PI of the rehydrated liposomal suspension 1 hour after reconstitution is preferably smaller than 0.4, more preferably smaller than 0.3, most preferably smaller than 0.25. Preferably the PI of said suspensions does only slightly change over 24 hours at 25° C., as described above.

In a special embodiment, the invention relates to an rehydrated aqueous liposomal suspension comprising cationic liposomes comprising up to about 5 mole %, preferably up to about 3 mole % paclitaxel in the liposomal membranes, wherein the PI of the liposomal suspension 1 hour after reconstitution is smaller than 0.4, more preferably smaller than 0.3, most preferably smaller than 0.25 and furthermore characterized by changes of the $Z_{average}$ by not more than a factor of about 1.5, preferably not more than 1.25, and changes of the PI value by not more that a factor of about 2, preferably not more than about 1.5, most preferably not more than about 1.25 over 24 hours at 25° C.

Preferably the liposomes of the above described rehydrated liposomal suspension do not release more than about 2% by weight, preferably not more than about 1% by weight, paclitaxel (based on the total weight of paclitaxel) from the liposomal membranes into the aqueous medium within 24 hours at 25° C.

FIGURE LEGENDS

FIG. 1: Amount of paclitaxel solubilised by liposome preparations with a lipid concentration of 10 mM and a total trehalose concentration of 10% (w/w). The liposomes were obtained from concentrated precursor formulations by dilution with water. The abscissa shows the initial concentration, i.e., the data at 10% trehalose were obtained from a suspension which was not diluted, and the data at 40% trehalose were obtained from an undiluted suspension which was originally 40% (w/w) in trehalose, and 40 mM in lipid, and which was diluted 1+3 with water.

Figure 2:
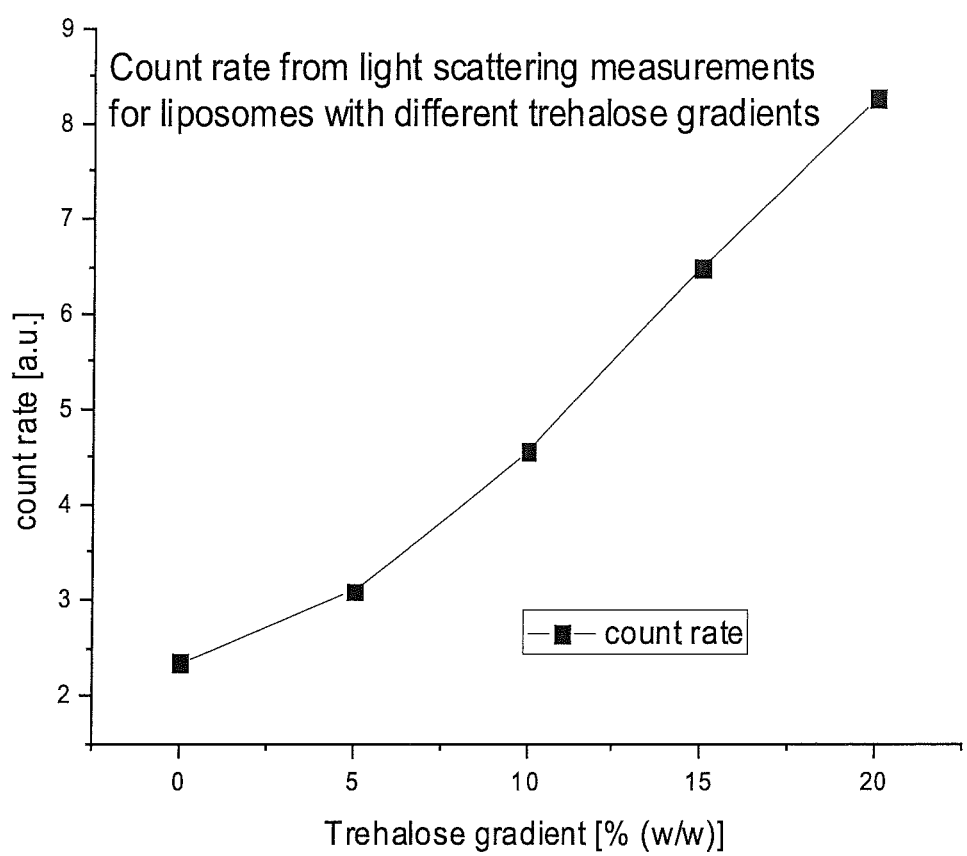

FIG. 2: Count rate of 10 mM DOTAP/DOPC liposomes obtained from a concentrated formulation of 30 mM lipid in 30% (w/w) trehalose. The solution was diluted with water/trehalose mixtures to different overall trehalose concentration between 30% and 10% (w/w). All formulations had the same final lipid concentration of 10 mM, but the trehalose concentration gradient between encapsulated and free aqueous phase was as indicated by the x-axis.

EXAMPLES

Loading of Paclitaxel to Liposomes with Different Trehalose Gradients

Summary

The effect of osmolar gradients on the partitioning of paclitaxel in liposomes at equilibrium with a saturated aqueous phase was investigated. Liposomes with different osmolar gradients were produced and incubated to paclitaxel crystals. All formulations had the same composition; more precisely, the lipid concentration and the trehalose concentration were $c_{lipid}$=10 mM and $c_{trehalose}$=10% (w/w). Some of the formulations were prepared and extruded at higher lipid and trehalose concentration, and diluted with water after extrusion to the final concentration. In this way, the free aqueous phase was diluted, but the encapsulated aqueous phase was not diluted (neglecting swelling effects and solute exchange through defects). An osmolar gradient between the encapsulated and the free aqueous phase was established, which increased with increasing dilution. The so formed liposomes were incubated with dry paclitaxel and the amount of paclitaxel which was solubilised by the liposomes was determined. A monotonous increase of solubilised paclitaxel with increasing dilution (concentration gradient) was found. The results indicate that the amount of paclitaxel which partitions in the liposome membrane at equilibrium increases with increasing osmolar gradient.

| MATERIALS | |
|---|---|
| Paclitaxel, Lot 06/150 | Cedarburg Pharmaceuticals |
| DOTAP, Lot MBA 113 | Merck Eprova |
| DOPC, Lot G181PC49 | Avanti Polar Lipids |
| Water, Milli-Q-Synthesis | Millipore |
| Trehalose-Dihydrate, highly pure | Senn Chemicals |
| Chloroform, p.a. | Merck |
| Acetonitrile, HPLC grade (ACN) | Merck |
| Tetrahydrofuran, HPLC grade (THF) | Merck |
| Ammonium acetate, p.a. | Merck |
| Trifluoroacetic acid, p.a. | Merck |
| Syringe filter minisart 0.2 μm pore size, 25 mm diameter Membrane: Cellulose acetate | Sartorius |
| HPLC System 1100 Degasser (G1379A) Binary Pump (G1312A) Thermostated autosampler (Autoinjektor G1329A, Thermostat G1330B) Thermostated column compartment (G1316A) Diode array detector (G1315B) or variable wavelength detector (G1314A) ChemStation for LC 3D, Rev. A.09.01 | Agilent |
| Extruder, 10 ml | Northern Lipids |
| Zetasizer 3000 | Malvern Instruments |

Methods

Preparation of Empty Liposomes

DOTAP/DOPC-formulations (1:1 ratio), or formulations comprising only DOTAP or DOPC, were prepared by the film method. The required amounts of lipids were weighed into a round flask and dissolved in chloroform. The solvent was evaporated to dryness in a rotary evaporator (Heidolph, Germany) at a pressure of about 150 mbar at a temperature of about 40° C. for about 15 minutes. The film was dried at 10 mbar over 60 minutes and subsequently hydrated in a trehalose solution in water by gently shaking the flask. Amounts of lipids, trehalose concentration and volume of trehalose solution were chosen to result in suspensions comprising lipid concentrations between 10 mM to 40 mM and trehalose concentrations between 9.8% and 39.2% (w/v) for DOTAP/DOPC-formulations and between 10 mM to 30 mM lipid concentration and between 9.8% and 29.4% (w/v) trehalose concentrations for DOTAP or DOPC only formulations. The resulting suspensions of multilamellar liposomes were extruded five times through a polycarbonate membrane of a pore size of 200 nm at a pressure of about 5 bar. After extrusion, the suspensions were diluted with water to yield suspensions with a lipid concentrations of 10 mM and a total trehalose concentration of 9.8% (w/v).

Paclitaxel Loading 5 ml of the suspensions comprising empty liposomes prepared as described above were added to 2.6 mg dry paclitaxel (corresponding to a theoretical paclitaxel concentration of 600 μM) in 15 ml Falcon tubes. The batches were stirred for 1 h at room temperature (magnetic stirrer).

After stirring, non liposomal bound paclitaxel was separated by filtration of 2 ml of each batch through a syringe filter (Sartorius minisart, 0.2 μm, cellulose acetate membrane). Paclitaxel- and lipid concentration in the resulting filtrates was subsequently analysed by HPLC.

Analytical Methods

Determination of Paclitaxel Content

Samples were diluted in ACN/THF/2 mM ammonium acetate 48/18/34 (v/v/v).

Stationary phase: LiChroCART® 250-4; LiChrospher 60, RP-select B length 250 mm, ID: 4 mm, particle size 5 μm Mobile phase: ACN/THF/2 mM ammonium acetate 32/12/56 (v/v/v)

Flowrate: 1 ml/min

Temperature column compartment: 35° C.

Detector wavelength: 229 nm

Injected volume: 10 μl

Runtime: 40 min

Determination of Lipid Content

The lipid content of the batches before and after filtration was analysed by HPLC to monitor a potential loss of liposomal material by the filtration process. Samples were diluted in ACN/water 50/50.

Stationary phase: Phenomenex Luna 5μ C8(2) 100 Å, 150 mm×2 mm

Mobile phase: Acetonitrile with 0.1% TFA, water with 0.1% TFA

Gradient Lipid Determination;

| time (min) | ACN (%) |
|---|---|
| 0 | 50 |
| 4.12 | 50 |
| 7.06 | 75 |
| 14.13 | 100 |
| 21.20 | 100 |
| 23.56 | 50 |
| 30.00 | 50 |

Flowrate: 0.4 ml/min

Temperature column compartment: 45° C.

Detector wavelength: 205 nm

Injected volume: 5 μl

Runtime: 30 min

Results

DOTAP/DOPC-Formulations

In FIG. 1 the amount of paclitaxel which was solubilised by incubation with different DOTAP/DOPC liposome formulations is shown. All formulations contained the same amount of lipid (liposomes) and trehalose. They were obtained from different more concentrated formulations by dilution with water. Except of the absolute concentration, all originating formulations were equivalent and they were treated equally. The abscissa gives the initial trehalose concentration, before dilution. Because in all cases the final overall trehalose concentration was 10%, the trehalose gradient increases with increasing values of the abscissa. As can be seen, the amount of paclitaxel which was solubilised by the liposomes increased monotonously with the trehalose gradient (dilution). The loading capacity of the liposomes increased with increasing trehalose gradient.

DOTAP- and DOPC-Formulations

The following table shows the amount of paclitaxel solubilised by DOTAP and DOPC liposome formulations (single components) in dependence of the initial trehalose concentration used for preparation:

TABLE 1

| DOTAP- and DOPC-formulations | | |
|---|---|---|
| $c_0$ trehalose | Paclitaxel concentration (μM) | |
| (%) | DOTAP | DOPC |
| 9.8 | 163 | 159 |
| 12.3 | 192 | 167 |
| 14.7 | 225 | 192 |

TABLE 1-continued

DOTAP- and DOPC-formulations

| $c_0$ trehalose | Paclitaxel concentration (μM) | |
|---|---|---|
| (%) | DOTAP | DOPC |
| 17.2 | 297 | 224 |
| 19.6 | 289 | 217 |
| 24.5 | 297 | 289 |
| 29.4 | 339 | 221 |

Also for the liposomes from pure lipid a clear dependence on the solubilisation capacity from the trehalose gradient was found. For DOTAP formulations, an increase of the paclitaxel loading capacity with an increasing trehalose concentration difference inside and outside the liposome comparable to the results for DOPTAP/DOPC formulations was observed. The effect was less pronounced liposomes consisting of 100% DOPC.

2 Loading of Paclitaxel to Liposomes with Different Trehalose Gradients After Spray-Drying 2.1 Summary Aim of this example was to test if the positive effect of the osmotic gradient on the paclitaxel loading to liposomes is present if the liposomes are spray dried between formation and adjustment of the trehalose gradient. DOTAP/DOPC liposomes were prepared at two different concentrations, namely 10 mM lipid in 10% (w/w) trehalose solution and 20 mM lipid in 20% (w/w) trehalose solution. Both formulations were spray dried at the respective concentration. The spray dried powders were both reconstituted with water to a lipid concentration of 10 mM and a corresponding trehalose concentration of 10% (w/w). The liquid formulations were exposed to paclitaxel as described above, and the amount of solubilised paclitaxel was determined. It was found, that the formulation which was spray dried from the double concentrated state (20 mM lipid/20% (w/w) trehalose) formulation solubilized more paclitaxel than the one, which was spray dried form the single concentrated state (10 mM lipid, 10% w/w trehalose).

The results indicate that the trehalose distribution inside/outside the liposomes was not affected by spray drying under the selected conditions. After reconstitution of the formerly double concentrated product, liposomes with a trehalose concentration gradient were obtained, correspondingly to the effect of direct dilution of the liquid formulation.

2.2 Methods

Liposome Formation

The formulations were prepared by ethanol injection. The appropriate amounts of lipid solution in ethanol (200 mM DOTAP-Cl, 188 mM DOPC) were injected under stirring into a solution of trehalose in water. The trehalose concentration was 20% (w/w) for the 20 mM liposomes and 10% (w/w) for the 10 mM liposomes. The required amount of lipid solution in ethanol was about 2.5 ml/l for the 10 mM formulation and 5 ml for the 20 mM formulation.

The resulting polydisperse liposomes formulations were extruded five times across polycarbonate membranes of 200 nm pore size at a pressure of about 5 bar.

Spray Drying

Spray Drying was performed with a Niro SD micro spray dryer using a two fluid nozzle. Spraying conditions were as follows: Outlet temperature=100° C., inlet temperature=145° C., feed rate=340 g/h, atomizer gas rate 2.3 kg/h, drying gas rate 30 kg/h.

Reconstitution

The dry powders, both from the previously 10 mM and the previously 20 mM formulation, were reconstituted with water to the lipid concentration of 10 mM.

Paclitaxel Loading Assay

Paclitaxel loading to the liposomes was performed as described in Example 1.

2.3 Results

The results as obtained from the paclitaxel loading to the reconstituted powders are shown in table 2. As can be seen the formulation which was spray dried at 20 mM lipid concentration solubilised much more paclitaxel than the formulation with the initial lipid concentration of 10 mM. It is concluded, that the elevated paclitaxel loading for the formerly 20 mM formulation was due to an osmolar gradient between encapsulated and free aqueous phase, which was not present in the formerly 10 mM formulation. Spray drying and reconstitution of the dry powder did not lead to trehalose equilibration between the interior and the exterior aqueous phase and therefore the osmolarity of the encapsulated aqueous phase was higher in case of the formerly 20 mM formulation.

Table 2: Solubilisation of paclitaxel by formulations obtained by reconstitution of spray dried powders. The lipid and trehalose concentration was identical in both cases (10 mM lipid, 10% w/w trehalose), but before spray drying one formulation was 10 mM lipid, 10% trehalose and the other formulation was 20 mM lipid, 20% trehalose.

| Initial lipid concentration of the formulation | Concentration of solubilised paclitaxel |
|---|---|
| 10 mM (PD_L_07030) | 164 (μM) |
| 20 mM (PD_L_07031) | 340 (μM) |

3. Stability of Loaded Liposomes 3.1 Summary

To evaluate the question, whether liposome preparations with an inside/outside trehalose gradient not only have a higher loading capacity, but also a greater stability with regard to the release of paclitaxel, the release of paclitaxel from the liposomes was traced as a function of time. Formulations with a relatively high paclitaxel fraction, namely 5 mol %, and with different trehalose gradients between 0% and 20% (w/w) were prepared. Liposomes comprising a trehalose gradient did not show any substantial paclitaxel release within the tested period of 21 days, while in liposomes without a trehalose gradient, the retained fraction of paclitaxel decreased to less than 1%.

3.2 Method

DOTAP/DOPC Formulations

DOTAP/DOPC liposomes comprising about 5 mol % paclitaxel (for exact values see table), 10 to 30 mM lipids, and 9.8% to 29.4% (w/v) trehalose were prepared according to the above described film method by adding the respective amount of lipids and paclitaxel to the chloroform solution. Subsequently the 30 mM batches were diluted to a lipid concentration of 10 mM (overall trehalose concentration 9.8% w/v) with water.

The samples were stored at 4° C. and the paclitaxel content of the liposomes was determined after 0, 1, 5, 14, and 21 days by the above described method using filtration and HPLC analysis.

3.3 Results

The results are summarized in Table 3. The concentration of paclitaxel (μm) retained in the liposomes is shown. The lipid concentration was 10 mM, therefore, the paclitaxel concentration of 100 µM corresponds to a molar concentration with respect to lipid of 1%.

In the formulation without trehalose gradient, the retained trehalose fraction monotonously decayed of to a value of less that 100 µM (less than 1 mol % with respect to lipid) after 21 days. In contrary, with trehalose gradient the retained paclitaxel did not fall below 400 µM. No monotonous decay was observed in that case, in other words, it appears that the value of about 400 µM represents a physically stable state of paclitaxel in the liposomes.

TABLE 3

Retention of paclitaxel in DOTAP/DOPC liposomes.

| | trehalose concentration gradient | | |
|---|---|---|---|
| | 0 | 10% | 20% |
| | Liposomally retained paclitaxel (µM) before filtration | | |
| t (d) after filtration | 470 | 444 | 425 |
| 0 | 453 | 446 | 411 |
| 1 | 438 | 428 | 407 |
| 5 | 391 | 429 | 420 |
| 14 | 90 | 427 | 412 |
| 21 | 79 | 409 | 400 |

The final fractions of retained paclitaxel are similar to the values as obtained from the loading assay for equivalently treated liposomes. Therefore, the data from the loading assay can be taken as predictive for the stability limit of loaded liposomes. If no other effects take place, the numbers from the loading assay will give information about the amount of paclitaxel which is retained by the liposomes under the given conditions. As a further conclusion from the present examples, it appears that the trehalose gradient, and the improved stability, is fully maintained for several days. In the present case, the effect was maintained for 21 days.

4 Methods for Determination of Trehalose Gradients in Liposome Preparations In Situ 4.1 Summary Concentrated liposome formulations in trehalose at a concentration $c_1$ were prepared and diluted either with water or with trehalose solution in different ratios to obtain media with trehalose concentration $c_2$, where $c_2 \leq c_1$. All formulations had the same final lipid concentration of 10 mM. The formulations were analysed based on local changes of optical properties (refractive index). Count rates of dynamic light scattering measurements were used to demonstrate the changes of scattering intensity. With increasing trehalose gradient, $c_1-c_2$, the count rate of dynamic light scattering (PCS) measurements monotonously increased.

4.2 Method

Dynamic light scattering was measured with a goniometer BI-200SM from Brookhaven Instruments (Holtsville USA). Measurements were performed with a 30 mW laser of a of 641 nm wavelength at an angle of 90°. For data analysis inverse Laplace transformation with optimize regularization techniques was performed.

4.3 Samples

DOTAP/DOPC (molar ration 1:1) liposomes with a total lipid concentration of 30 mM were prepared in a solution of 30% trehalose. The 30 mM lipid 30% trehalose liposome preparation was extruded across 200 extrusion membranes. Subsequently, the liposomes were diluted with water, 30% trehalose solution or mixtures thereof in ratios as indicated in the table.

A: 30 mM liposomes in 30% trehalose
B: 30% trehalose in water
C: Water

TABLE 4

Dilution protocol for 10 mM lipid formulations in an aqueous phase with trehalose at concentrations between 10% and 30% (w/w)

| # | Vol. A | Vol. B | Vol. C | Final composition |
|---|---|---|---|---|
| 1 | 1 | 2 | — | 10 mM liposomes in 30% trehalose |
| 2 | 1 | 1.5 | 0.5 | 10 mM liposomes in 25% trehalose |
| 3 | 1 | 1 | 1 | 10 mM liposomes in 20% trehalose |
| 4 | 1 | 0.5 | 1.5 | 10 mM liposomes in 15% trehalose |
| 5 | 1 | — | 2 | 10 mM liposomes in 10% trehalose |

The lipid concentration in the final preparation was always 10 mM, but the overall trehalose concentration varied between 10% (dilution with water) and 30% (dilution with 30% trehalose solution). With the initial trehalose concentration of 30%, this resulted in a numerical trehalose concentration gradient between 0% (total concentration=30%) and 20% (total concentration=10%). One hour after dilution, Dynamic light scattering measurement was performed.

4.4 Results

FIG. 2 shows results of the dynamic light scattering measurements. The count rate is given as a function of trehalose gradient. The count rate monotonously increased with increasing trehalose gradient. This can be correlated to the increase of refractive index gradient and swelling effects on increasing trehalose gradient. It is well known, that liposomes can act as ideal osmometers, and osmolar gradients can be determined from light scattering and light absorption properties under suitable conditions (de Gier 1993; Cabral, Hennies et al. 2003). Besides the intensity from quasi elastic light scattering, also other light scattering techniques as well as absorption or turbidimetry measurements can be used. The present observations indicate that analyzing the count rate in dynamic light scattering measurements can be used as a tool to control success of trehalose gradient formation for a given formulation. Furthermore the data confirm that the change of the osmolarity of the aqueous medium of a liposomal suspension renders the physical properties of the liposomes.

5 Influence of a Trehalose Gradient on the Physical Stability of Liquid DOTAP/DOPC Liposome Formulations of Paclitaxel 5.1 Summary In this example the stabilizing effect of trehalose gradients on DOTAP/DOPC liposome formulations of paclitaxel as shown by Example 3 was further investigated. Liposomes were prepared at a concentration of 30 mM (in 32% w/w trehalose solution), diluted with different trehalose/water solutions, and paclitaxel release after mechanical stress was determined.

It was found, that the physical stability increased with increasing trehalose gradient. The findings confirmed the stabilizing effect of trehalose gradients on paclitaxel comprising liposomes also for processing at pilot scale.

5.2 Methods and Materials

Liposome Manufacturing

Liposomes were produced by the ethanol injection technique. Briefly, a solution of 200 mM DOTAP and 188 mM DOPC (total lipid concentration 388 mM) was injected under stirring at a temperature of 2-8° C. into the aqueous phase (8.11 ml of lipid solution in ethanol for 100 ml of aqueous phase) to yield polydisperse liposomes with a lipid concentration of about 30 mM. For the aqueous phase a solution of 32.1% w/w trehalose dihydrate with 184.5 µM citric acid was selected.

Extrusion was performed as indicated at a pressure of 3 bar with polycarbonate membranes of 220 nm pore size. Sterile fitration was performed as indicated using milipak 20 sterile filters or durapore membranes (Millipore, Molsheim, France).

Concentration Gradients

The initial 30 mM liposome formulations in 30% (w/w) trehalose solution (PD-L-09111) was diluted with water to different final lipid and trehalose concentrations.

TABLE 5

Dilution of tested samples

| Name | PD-L-09111 (ml) | Water (ml) | $C_{lipid}$ (mM) | C trehalose (% w/w) | Δc trehalose (% w/w) |
|---|---|---|---|---|---|
| PD-L-09111 | 100 | 0 | 30 | 30 | 0 |
| PD-L-09112 | 70 | 70 | 15 | 15 | 15 |
| PD-L-09113 | 90 | 54 | 18.8 | 18.8 | 11.2 |
| PD-L-09114 | 100 | 0 | 30 | 30 | 0 |
| PD-L-09115 | 80 | 64 | 16.7 | 16.7 | 13.3 |
| PD-L-09116 | 100 | 40 | 21.4 | 21.4 | 8.6 |
| PD-L-09119 | 100 | 24 | 25 | 25 | 5 |

Stability Testing

The samples were put on a shaker and agitated at 150 rpm at 25° C. or at 2-8° C., respectively. After 24 and 48 hours the samples were analyzed and the amount of paclitaxel retained in the liposomes was determined.

Determination of Paclitaxel Retention/Release in the Liposomes Preparations

Paclitaxel retention in liposomes was investigated by filtration of the liposome preparations in order to remove paclitaxel crystals from the liposome product (as described in Example 3). The remaining paclitaxel was quantified by HPLC analysis. Additionally, optical microscopy was used to investigate the samples for paclitaxel crystals.

5.3 Results

Results are given in Tables 6-12. For simplicity, the initial concentration of trehalose is approximated as 30% (w/w). Concentration gradients as depicted are calculated from the initial trehalose concentration and the dilution factor. The actual concentration gradients between encapsulated and free aqueous phase will have the same trend, but the absolute values may differ slightly from those given in the tables.

As can be seen, the stability increases with increasing trehalose gradient. The amount of liposomally retained paclitaxel increases and less paclitaxel crystals are observed. The stability is higher at 5° C. compared to 25° C.

TABLE 6

Stability at 0% trehalose gradient

| Particle number | | Temp | time | PXL lost on filtration | Crystals in |
|---|---|---|---|---|---|
| >1 µM | >1 µM >25 µM | (° C.) | (h) | (%) | microscopy |
| PD-L-09111 | 30 0 | 5 | 24 | <5 | No |
| PD-L-09111 | 30 0 | 5 | 24 | 8 | Yes |
| PD-L-09111 | 30 0 | 5 | 48 | 8 | Yes |
| PD-L-09111 | 30 0 | 5 | 48 | 19 | Yes |
| PD-L-09111 | 30 0 | 25 | 24 | 86 | Yes |
| PD-L-09111 | 30 0 | 25 | 24 | 86 | Yes |

TABLE 6-continued

Stability at 0% trehalose gradient

| Particle number | | Temp | time | PXL lost on filtration | Crystals in |
|---|---|---|---|---|---|
| >1 µM | >1 µM >25 µM | (° C.) | (h) | (%) | microscopy |
| PD-L-09111 | 30 0 | 25 | 48 | 85 | Yes |
| PD-L-09111 | 30 0 | 25 | 48 | 85 | Yes |

TABLE 7

Stability at 5% trehalose gradient

| Sample | $C_{lipid}$ (mM) | Δ $C_{tre}$ (% w/w) | Temp (° C.) | time (h) | PXL lost on filtration (%) | Crystals in microscopy |
|---|---|---|---|---|---|---|
| PD-L-09119 | 25 | 5 | 5 | 24 | <5 | No |
| PD-L-09119 | 25 | 5 | 5 | 24 | <5 | No |
| PD-L-09119 | 25 | 5 | 5 | 48 | <5 | No |
| PD-L-09119 | 25 | 5 | 5 | 48 | <5 | No |
| PD-L-09119 | 25 | 5 | 25 | 24 | 29 | Yes |
| PD-L-09119 | 25 | 5 | 25 | 24 | 44 | Yes |
| PD-L-09119 | 25 | 5 | 25 | 48 | 70 | Yes |
| PD-L-09119 | 25 | 5 | 25 | 48 | 69 | Yes |

TABLE 8

Stability at 8.6% trehalose gradient

| Sample | $C_{lipid}$ (mM) | Δ $C_{tre}$ (% w/w) | temp (° C.) | time (h) | PXL lost on filtration (%) | Crystals in microscopy |
|---|---|---|---|---|---|---|
| PD-L-09116 | 21.4 | 8.6 | 5 | 24 | <5 | No |
| PD-L-09116 | 21.4 | 8.6 | 5 | 24 | <5 | No |
| PD-L-09116 | 21.4 | 8.6 | 5 | 48 | <5 | No |
| PD-L-09116 | 21.4 | 8.6 | 5 | 48 | <5 | No |
| PD-L-09116 | 21.4 | 8.6 | 40 | 24 | <5 | No |
| PD-L-09116 | 21.4 | 8.6 | 40 | 24 | <5 | No |
| PD-L-09116 | 21.4 | 8.6 | 40 | 48 | <5 | Yes |
| PD-L-09116 | 21.4 | 8.6 | 40 | 48 | <5 | Yes |

TABLE 9

Stability at 11.2% trehalose gradient

| Sample | $C_{lipid}$ (mM) | Δ $C_{tre}$ (% w/w) | temp (° C.) | time (h) | PXL lost on filtration (%) | Crystals in microscopy |
|---|---|---|---|---|---|---|
| PD-L-09113 | 18.8 | 11.2 | 5 | 24 | <5 | No |
| PD-L-09113 | 18.8 | 11.2 | 5 | 24 | <5 | No |
| PD-L-09113 | 18.8 | 11.2 | 5 | 48 | <5 | No |
| PD-L-09113 | 18.8 | 11.2 | 5 | 48 | <5 | No |
| PD-L-09113 | 18.8 | 11.2 | 40 | 24 | <5 | No |
| PD-L-09113 | 18.8 | 11.2 | 40 | 24 | <5 | No |
| PD-L-09113 | 18.8 | 11.2 | 40 | 48 | <5 | No |
| PD-L-09113 | 18.8 | 11.2 | 40 | 48 | <5 | No |

TABLE 10

Stability at 13.3% trehalose gradient

| Sample | $C_{lipid}$ (mM) | Δ $C_{tre}$ (% w/w) | temp (° C.) | time (h) | PXL lost on filtration (%) | Crystals in microscopy |
|---|---|---|---|---|---|---|
| PD-L-09115 | 16.7 | 13.3 | 5 | 24 | <5 | No |
| PD-L-09115 | 16.7 | 13.3 | 5 | 24 | <5 | No |

TABLE 10-continued

Stability at 13.3% trehalose gradient

| Sample | $C_{lipid}$ (mM) | $\Delta C_{tre}$ (% w/w) | temp (° C.) | time (h) | PXL lost on filtration (%) | Crystals in microscopy |
|---|---|---|---|---|---|---|
| PD-L-09115 | 16.7 | 13.3 | 5 | 48 | <5 | No |
| PD-L-09115 | 16.7 | 13.3 | 5 | 48 | <5 | No |
| PD-L-09115 | 16.7 | 13.3 | 40 | 24 | <5 | No |
| PD-L-09115 | 16.7 | 13.3 | 40 | 24 | <5 | No |
| PD-L-09115 | 16.7 | 13.3 | 40 | 48 | <5 | No |
| PD-L-09115 | 16.7 | 13.3 | 40 | 48 | <5 | No |

TABLE 11

Stability at 13.3% trehalose gradient

| Sample | $C_{lipid}$ (mM) | $\Delta C_{tre}$ (% w/w) | temp (° C.) | time (h) | PXL lost on filtration (%) | Crystals in microscopy |
|---|---|---|---|---|---|---|
| PD-L-09115 | 16.7 | 13.3 | 5 | 24 | <5 | No |
| PD-L-09115 | 16.7 | 13.3 | 5 | 24 | <5 | No |
| PD-L-09115 | 16.7 | 13.3 | 5 | 48 | <5 | No |
| PD-L-09115 | 16.7 | 13.3 | 5 | 48 | <5 | No |
| PD-L-09115 | 16.7 | 13.3 | 40 | 24 | <5 | No |
| PD-L-09115 | 16.7 | 13.3 | 40 | 24 | <5 | No |
| PD-L-09115 | 16.7 | 13.3 | 40 | 48 | <5 | No |
| PD-L-09115 | 16.7 | 13.3 | 40 | 48 | <5 | No |

TABLE 12

Stability at 15% trehalose gradient

| Sample | $C_{lipid}$ (mM) | $\Delta C_{tre}$ (% w/w) | temp (° C.) | time (h) | PXL lost on filtration (%) | Crystals in microscopy |
|---|---|---|---|---|---|---|
| PD-L-09112 | 15 | 15 | 5 | 24 | <5 | No |
| PD-L-09112 | 15 | 15 | 5 | 24 | <5 | No |
| PD-L-09112 | 15 | 15 | 5 | 48 | <5 | No |
| PD-L-09112 | 15 | 15 | 5 | 48 | <5 | No |
| PD-L-09112 | 15 | 15 | 40 | 24 | <5 | No |
| PD-L-09112 | 15 | 15 | 40 | 24 | <5 | No |
| PD-L-09112 | 15 | 15 | 40 | 48 | <5 | No |
| PD-L-09112 | 15 | 15 | 40 | 48 | <5 | No |

6 Stability of Spray-Dried Paclitaxel-Loaded Liposomes
6.1 Methods and Materials Materials were used as described in the previous examples.

Liposomes consisting of DOTAP, DOPC and paclitaxel (molar ratio 50/47/3) were formed by the ethanol injection techniques as described above. The paclitaxel was solubilised with the lipids in the ethanol solution. Liposomes at a concentration of 20 mM lipid in 20% w/w trehalose (batch PD-L-09031) and 10 mM lipid in 10% trehalose (batches MDG09.108-08-001 and PD-L-09032) were prepared. The liposomes were extruded five times across polycarbonate membranes of 200 nm pore size and sterile filtrated as described above.

After preparation of the liposomal suspensions, the liposomes were dehydrated. Batches PD-L-09031 and PD-L-09031 were spray dried in a Niro SD-Micro spray dryer with spray drying parameters as described in Example 2.

Batch MDG09.108-08-001 was dehydrated by freeze drying, using a Epsilon 2-12D (Christ) freeze drying unit. The liposomal suspension was kept at 4° C. for 1 hour and frozen at −40° C. for about 5 hours. After freezing, temperature was increased to −16° C. and primary drying was performed at a pressure of 0.1 bar for 90 hours. For secondary drying, the temperature was increased to 20° C., while pressure was reduced to 0.01 bar.

The dry powders were reconstituted with water to a lipid concentration of 10 mM in 10.5% (w/w) trehalose. The resulting liquid liposome products were investigated one hour after reconstitution and 24 hours after reconstitution with dynamic lights scattering measurements using a using a Malvern Zetasizer 1000HSA, Series DTS5101 (Settings: Analysis=mono modal, Dilation=1.2; Order of fit=3; Point selection First=18; Last Point Selection=By Number 22; Point weighting=quatric; Attenuator=×16; Viscosity 1.200 cp; Refractive Index=1,348; Number of Measurements=3; Delay Between Measurements=0; Measurement Duration=Auto) to determine $Z_{ave}$ and PI. Before measurement the samples were diluted ten-fold with 10.5% (w/w) trehalose dehydrate solution.

6.2 Results

The results are shown in Table 13.

The findings for the formulation which was spray dried at the same lipid and trehalose concentration as in the rehydrated product were substantial different from the results for the product which had been sprayed from double concentrated liquid feed and a trehalose gradient had been generated upon rehydration. The formulation without concentration gradient displayed significantly higher $Z_{ave}$ and PI values and increased within 24 hours after reconstitution, while the formulation with concentration gradient did not show such increase. The increase in $Z_{ave}$ and PI is considered to be related to paclitaxel release from the formulation without concentration gradient, which was less stable. The data are in accordance with the results of Example 2, where more paclitaxel could be loaded to liposomes which had been obtained after spray drying at double concentration and subsequent generation of a trehalose gradient. Spray drying of the paclitaxel liposome formulations at higher trehalose concentrations and subsequent generation of a trehalose gradient improves the stability of the formulation after reconstitution.

In comparison to the spray dried samples, the freeze dried formulation showed a much higher PI already after reconstitution.

TABLE 13

Comparison of dehydration and rehydration methods

| Batch | $\Delta c_{trehalose}$ | 1 h $Z_{ave}$ (nm) | 1 h PI | 24 h $Z_{ave}$ (nm) | 24 h PI |
|---|---|---|---|---|---|
| MDG09.108-08-001 | 0% | 170.3 | 0.480 | 175.4 | 0.493 |
| PD-L-09032 | 0% | 167 | 0.331 | 260 | 0.65 |
| PD-L-09031 | 10% | 160.8 | 0.203 | 160.5 | 0.199 |

7 Large Scale Manufacturing and Spray Drying
7.1 Material
7.1.1 Basic Materials
USP Semi-Synthetic Paclitaxel API, Phyton Biotech, Lot CP209N0014
DOTAP-Cl, Merck Eprova AG, Lot MBA-020
DOPC, Avanti Polar Lipids Inc., Lot GN181 PC-12
α,α-Trehalose Dihydrate High Purity (Low Endotoxine), Ferro Pfanstiehl, Lot 33205A
Ethanol absolute EP, Nova Laboratories Art.-Nr. A4478B
Citric acid monohydrate EP/USP, Nova Laboratories Art.-Nr. V290
Water for injection, Nova Laboratories Art.-Nr. A15210C

7.1.2 Equipment

Injection capillary ID: 2 mm
Filter cartridge Memtrex PC 0.2 pm from GE, Article No. MPC92O5FHV, Lot. 60240937
Sterile filter Opticap XL4 with 0.22 pm Duraporemembrane from Millipore, Article Nr. KVGLAO4TT3 Lot.: COCA1 0972
Formulation-Vessel (Nova Laboratories Ltd.)
Extrusion-Vessel (Nova Laboratories Ltd.)
Bioburden-Reduction-Vessel (Nova Laboratories Ltd.)
Holding-Vessel (Nova Laboratories Ltd.)
Peristaltic pump (Nova Laboratories Ltd.)
20 L-pressure vessel with standpipe (Nova Laboratories Ltd.)
Butterfly-vents (Nova Laboratories Ltd.)
ASD-1 aseptic spraydryer (GEA Niro S/A, Copenhagen Denmark)

7.2 Methods

7.2.1 Production of Liquid Formulation

7.2.1.1 Preparation of Organic Solution

For batch 001, 349.3 g DOTAP-CL were dissolved in solved in 700 g absolute ethanol and stirred for approximately 4 h. 369.5 g DOPC was dissolved in 700 g absolute ethanol and stirred for approximately 3 h. Subsequently the two lipid solutions were joined and added to 25.617 g paclitaxel. The resulting organic solution was stirred for about 2 hours and finally adjusted to a total weight of 2122.5 g by the addition of absolute ethanol. Batches 002 to 004 were prepares accordingly

7.2.1.2 Preparation of Aqueous Solution

For batch 001, 10819 g of trehalose dehydrate were added to about 20 kg of water for injection in a formulation vessel and stirred at 700 rpm for 90 min. Subsequently 1.258 g citric acid monohydrate were added and stirred until complete dissolution. The final volume of the aqueous solution was adjusted to 34.53 kg and stirred for another 10 min. Batches 002 to 004 were prepared accordingly

7.2.1.3 Ethanol Injection

For batch 001, the organic solution was injected into the aqueous solution by means of a peristaltic pump with an injection rate of about 250 g/min. During injection, the solution was stirred at about 500 rpm. After the injection was finished the solution was stirred for 2 min at 600 rpm and subsequently for 1 min at 700 rpm. During the whole injection process the temperature was kept below 8° C. Batches 002 to 004 were stirred at 550 rpm during injection with no additional stirring thereafter.

7.2.1.4 Extrusion 8 extrusions over a 5" filter cartridge with a 0.2 pm polycarbonatemembrane were performed. The filter cartridge was ventilated with 0.4-0.5 bar each, and extrusion was performed with a pressure of 3.0 bar. Temperature was kept below 8° C.

7.2.1.5 Dilution

After the 8th extrusion the weight of the formulation was determined. Based on the formulation's density of 1.106 g/ml the amount of water was calculated which was required to obtain a 20 mM formulation (based on total lipid concentration), which corresponds to a 1:1.5 dilution. For batch 001, the required amount of water for injection was added at 1.66 l/min by means of a peristaltic pump through a 2 mm ID capillary while the solution was stirred at about 500 rpm. The added water for injection had been chilled to below 8° C. before adding to the formulation. For batches 002 to 004 dilution was performed at 0.62 l/min to 0.83 l/min at a stirring speed of about 600 rpm.

7.2.1.6 Reduction of Bioburden

Before the reduction of bioburden (1'st sterile filtration), the OpticapXL4 filter was washed with 20 L water for injection at a pressure of about 0.5 bar. Filling and ventilation of the filter was performed gravimetrically. The filtration was performed at a pressure of 2.5 bar, whereby the pressure was applied promptly. Temperature of the formulation was kept below 8° C.

7.2.1.7 Sterile Filtration

Before the sterile filtration, the OpticapXL4 filter was washed with 20 L water for injection at a pressure of about 0.5 bar. Ventilation of the filter was performed at 0.5 bar. The filtration was performed at a pressure of 2.5 bar, whereby the pressure was applied promptly. Temperature of the formulation was kept below 8° C.

7.2.2 Spray-Drying

The liposomal formulation was spray dried in a ASD-1 aseptic spray-dryer (GEA Niro S/A, Copenhagen Denmark). Batch 001 was dried as single batch (Run 1), whereas batches 002 to 004 were sprayed sequentially in a continuous fashion (Run 2). For spray-drying a two-fluid nozzle, nitrogen as drying gas, and the following parameters were used:

TABLE 14

| spray drying settings | |
|---|---|
| Parameter | Set point |
| Drying gas rate | 80 kg/h |
| Atomizer-gas pressure | 3 bar |
| Atomizer-gas rate | 3 kg/h |
| Outlet temperature | 95° C. |
| Feed rate | 2 L/h |
| Feed temperature | 0° C.-30° C. |

7.3. Stability of Liposomes

7.3.1. Method

Dehydrated liposomal compositions from Run1 were rehydrated in water for injection to a total lipid concentration of 10 mM, thus the reconstitution conditions further increase the osmolar gradient of the preparation which had been 20 mM before dehydration. For comparison, a corresponding liposomal composition (Reference Batch) which was prepared without dilution and had been dehydrated by lyophilisation (as for example disclosed in WO 2004/002468). The amount of paclitaxel (including paclitaxel degradation products) retained in the liposomes was determined according to the method described in Example 1.3 after reconstitution of the liposomes and after 24 hours at 25° C. The percentage of paclitaxel retained and filterable (crystallised) paclitaxel was calculated based on the total paclitaxel present in the preparations.

7.3.2. Results

TABLE 15

| | Release of paclitaxel from products | | | |
|---|---|---|---|---|
| | T0 | | After 24 h at 25° C. | |
| Preparation Time | Liposomally retained paclitaxel [%] | Filterable paclitaxel [%] | Liposomally retained paclitaxel [%] | Filterable paclitaxel [%] |
| Run1 | 99.56 | 0.44 | 99.89 | 0.11 |
| | 99.93 | 0.07 | 100.09 | −0.09 |
| | 99.67 | 0.33 | 99.87 | 0.13 |

TABLE 15-continued

Release of paclitaxel from products

| Preparation Time | T0 | | After 24 h at 25° C. | |
|---|---|---|---|---|
| | Liposomally retained paclitaxel [%] | Filterable paclitaxel [%] | Liposomally retained paclitaxel [%] | Filterable paclitaxel [%] |
| Reference Batch | 99.63 | 0.37 | 98.88 | 1.12 |
| | 99.48 | 0.52 | 98.68 | 1.32 |
| | 99.72 | 0.28 | 99.16 | 0.84 |

The data show that liposomal preparations prepared in the absence of an osmolar gradient release paclitaxel faster. This can already be observed after a relatively short time span of 24 h.

7.4. Analysis of Particle Size and Polydispersity 7.4.1. Methods

Particle size (zaverage) and polydispersity index (PI) were determined by PCS (173° diffraction) using a Zetasizer Nano ZS (Malvern Instruments). In brief, sampled from Run1 (corresponding to Batch 1) and Run2 (corresponding to Runs 2-4) and a sample form Reference Batch (see above) were resuspended in water to a total lipid concentration of 10 mM. For measurement the samples were diluted ten fold with 10.5% trehalose dehydrate solution (w/w). The samples were stored for 24 hours and 25° C. and measured again.

The following settings were used for measurement and data analysis: Measurement type=Size; Sample: Material=Polystyrene latex, RI: 1.590; Absorption: 0.01; Dispersant=10.5% Trehalose, Temperature: 25° C., Viscosity 1.200 cP RI: 1.342; General options=Mark-Houwink parameters; Temperature=25° C., Equilibration time: 5 minutes; Cell=DTS0012-Disposable sizing cuvette; Measurement: Number of runs=15; Run duration (seconds)=100; Number of measurements=3; Delay between measurements; Advanced=Fixed Position at Position 4.65, Attenuator 6; Analysis Parameters: Analysis mode=General; Cumulants analysis: Order of fit=3; Weighting scheme=Quadratic; Cumulants point selection: Automatic first point=Yes; Last point selection method=Cut-off; Fraction of signal=0.1; Dilation=1.2; Display range: Lower limit=0.6; Upper limit=10000; Filtering: Filter factor=75; Multimodal-analysis: Result transformation=Mie; Use result transformation=Yes; Weighting scheme=Quadratic; Resolution=normal; Multimodal—points selection; Automatic first point=Yes; Last point selection method=Cut-off Fraction of signal=0.01; Dilation=1.2; Size classes: Number of size classes=70; Lower limit=0.4; Upper limit=10000; Thresholds: Lower Threshold=0.05; Upper Threshold=0.01; Filter factor=default.

7.4.2. Results

The results are shown in Table 16:

| Sample | | zaverage (nm) | PI |
|---|---|---|---|
| Reference Batch | | 133 | 0.337 |
| Run 1 | Batch 1 | 143 | 0.16 |
| Run 2 | Batch 2 | 138 | 0.15 |
| | Batch 3 | 143 | 0.17 |
| | Batch 4 | 144 | 0.19 |

The formulations manufactured with an osmotic gradient and dehydrated by spray-drying (Runs 1 & 2) displayed a very similar zaverage but significantly lower PI values compared to the reference sample manufactured without an osmotic gradient and dehydrated by lyophilisation. Thus the product produced by the process described above is more homogeneous than a product produced by a conventional process.

7.5 Ultracentrifugation Characterisation 7.5.1. Method

Analysis of ultracentrifugation was performed by Nanolytics (Potsdam, Germany).

Each sample was reconstituted in $H_2O$ and a 1:1 mixture of $H_2O$: $D_2O$ to a lipid concentration of 10 mM and equilibrated for one hour at room temperature. Subsequently the samples were diluted 1:1 with the respective solvent. After another hour of equilibration the samples were subjected to ultracentrifugation. 400 µl of the respective liposomal dispersion were subjected to a titanium ultracentrifugation cuvette with an optical path of 12 mm. The samples were centrifuged in a Optima XL-I analytical ultracentrifuge (Beckmann-Coulter, Palo Alto) using an An50Ti 8-place rotor (Beckmann-Coulter, Palo Alto) equipped with Rayleigh interference optics at 20000 rpm and 25° C. During the centrifugation, the concentration profile along the radial coordinate was by means of the refractivity gradient within the solution. Samples were measured as duplicates.

7.5.2. Data Analysis 7.5.2.1 Definition of the Sedimentation Coefficient

The primary indicator in analytical ultracentrifugation is the sedimentation coefficient defined as follows:

$$\frac{m(1 - \bar{v}\varrho)}{f} = \frac{u}{\omega^2 r} \equiv s \quad (1)$$

Wherein u is the sedimentation velocity of the particle, m the mass of the particle, $\bar{v}$ is the specific volume, f is the friction term and ρ is the density of the solvent.

Determination of the Sedimentation Coefficient

The sedimentation coefficient is calculated directly from the measured data without further assumptions according to:

$$\ln\frac{r}{r_m} = s \int \omega^2 dt \quad (2)$$

Wherein r is the distance to the rotation axis, and $r_m$ is the meniscus. The run time integral $\int \omega^2 dt$ is determined by the measuring equipment.

7.5.2.3 Sedimentation Coefficient Distribution

Instead of a single sedimentation coefficient at a specific radius, the whole r-axis can be transformed into an s-axis. The fringe shift at the respective position is proportional to the mass concentration of the particle species present there, so that the measures amplitude can be taken as y-coordinate. However it is required to correct the y-coordinate with regard to the radial dilution. By including the correction term the following function g(s) is obtained, giving the mass concentration of the particle species sedimenting with velocity s:

$$g(s) = \frac{1}{c_0}\frac{dc}{dt}\left(\frac{r}{r_m}\right)^2 r \int \omega^2 dt \quad (3)$$

The concentration c, respectively c0 is given in units fringe shift, wherein a fringe equals a full phase, thus a light and a dark line of the interference pattern. The size is direct proportional to the concentration given in g/l in case the refractive index increment can be assumed to be equal for all particle species, which is the case for the present samples which are chemical uniform material which is simply present in a polydisperse distribution:

$$dc = d\phi \cdot \lambda \cdot \frac{1}{l \frac{dn}{dc}} \quad (4)$$

Wherein φ is the concentration in fringe shift units, λ is the wavelength of the laser, l the width of the cuvette, and dn/dc is the refractory index increment of the solute in a given solvent. Due to this proportionality the concentration in equation (3) can be stated directly as mass concentration.

g(s) (or its integrated form G(s) can in principle be calculated scan by scan coordinate transformation and calculation of the y-coordinate according to equation (3); the overall result would be obtained by averaging the mainly scans, which are mainly redundant. Thus it is reasonable to perform a global data fitting over all scans. Thereby time and space independent noise is isolated and further statistic noise is partitioned to obtain the best g(s) is obtained from the entire measurement data. SedFit v12.4. software from Peter Schuck was used for the fitting.

7.5.2.4 Interpretation of Sedimentation Coefficient Distribution

The sedimentation coefficient distribution in the form of the function g(s) already gives information on the from of the distribution; usually it is desirable to transform the primary measurement parameter s into the diameter or mass of the particle. The sedimentation coefficient is related to the molar mass by the SVEDBERG Equation $$M = \frac{sRT}{D(1 - \overline{v}\varrho)} \quad (5)$$

via the diffusion coefficient. For globular objects, as for the present liposomes, the diffusion coefficient can be replaced by the diameter of a sphere, whereby it has to be considered, that the liposome is filled with water, which does not contribute to the sedimentation but to the friction.

If the diffusion coefficient in equation 5 is replaced by the STOKES-EINSTEIN-Equation $$D = 6\pi\eta R_h \quad (6)$$

and considers the diameter d=2Rh for a sphere and a volume fraction of water Φ; the SVEDBERG Equation becomes $$d = \sqrt{\frac{18\eta s}{(1 - \Phi)(\varrho_s - \varrho)}} \quad (7)$$

wherein η is the viscosity of the solvent and $\rho_s$ is the density of the solute.

For the conversion of the sedimentation coefficient distribution into a size distribution it is required that the swelling and density of the liposomes remain constant or are given as a distribution dependent on the sedimentation coefficient. Thus the density is determined experimentally.

7.5.2.5 Analysis of the Density Variation

The density of sedimenting particles can be determined by analytical ultracentrifugation in two solvents with differing density. In the solvents having a lower density, a particle normally exhibits a smaller s-value—the particle sediments slower, if the density difference to the surrounding solvent decreases. Both s-values, which describe the same particle, fulfil equation (7) with the parameters for the respective solvent. For the two solvents (index 1 and 2) the following applies:

$$\frac{\eta_1 s_1}{[\Phi \varrho_1 + (1 - \Phi)\varrho_s] - \varrho_1} = \frac{\eta_2 s_2}{[\Phi \varrho_2 + (1 - \Phi)\varrho_s] - \varrho_2} \quad (8)$$

The anhydrous density of the particle $\rho_s$ and the swelling parameter Φ on both sides of the equation are identical, since they refer to the same object. Identical particles are defined as elements of the sedimentation coefficient distribution with identical y-coordinate G(s).

Thus equation (8) can be rearranged and simplified to obtain the anhydrous density:

$$\varrho_s = \frac{\eta_1 s_1 \varrho_2 - \eta_2 s_2 \varrho_1}{s_1 \eta_1 - s_2 \eta_2} \quad (9)$$

The diameter can be derived according to the following equation:

$$d = \sqrt{\frac{18(\eta_1 s_1 - \eta_2 s_2)}{(1 - \Phi) \cdot (\varrho_1 - \varrho_2)}} \quad (10)$$

To solve equation (10), independent information such as the diameter of the particles is required, which can be determined experimentally by dynamic light scattering experiments as described above.

7.5.3. Results

TABLE 17

Anhydrous density of liposomal preparation

| Manufacturing Run | Sample | Anhydrous density (g/ml) |
|---|---|---|
| Run 1 | Sample 1 | 1.183 |
| Run 2 | Sample 1 | 1.174 |
|  | Sample 2 | 1.154 |
|  | Sample 3 | 1.223 |

REFERENCES

Antonietti, M. and S. Forster (2003). "Vesicles and liposomes: A self-assembly principle beyond lipids." Advanced Materials 15(16): 1323-1333.

Bangham A. D., Standish M. M., Watkins, J. C. (1965). "Diffusion of univalent ions across the lamellae of swollen phospholipids", J. Mol. Biol. 13: 238-52.

Cabral, E. C. et al. (2003). "Preparation and characterization of diacetylene polymerized liposomes for detection of autoantibodies." J Liposome Res 13(3-4): 199-211.

De Gier, J. (1993). "Osmotic behaviour and permeability properties of liposomes." Chem Phys Lipids 64(1-3): 187-196.

Ertel, A., A. G. Marangoni, et al. (1993). "Mechanical properties of vesicles. I. Coordinated analysis of osmotic swelling and lysis." Biophysical Journal 64(2): 426-434.

Evans, D. F. and Wennerstrom H. (1994). "The Colloidal Domain", VHC Publishers, Inc., New York, pp 48-49.

Goormaghtigh, E. and G. A. Scarborough (1986). "Density-based separation of liposomes by glycerol gradient centrifugation." Anal Biochem 159(1): 122-31.

Gregoriadis G. (1995). "Engineering liposomes for drug delivery: Progress and problems". Trends in biotechnology 13 (12): 527-537.

Hallett, F. R., J. Marsh, et al. (1993). "Mechanical properties of vesicles. II. A model for osmotic swelling and lysis." Biophysical Journal 64(2): 435-442.

Huang, C. H., Charlton, J. P. (1971) "Determination of partial specific volumes by sedimentation velocity method", The Journal of Biological Chemistry, 246(8): 2555-2560.

Koppel, D. E. (1972). "Analysis of macromolecular polydispersity in intensity correlation spectroscopy: the method of cumulants." Journal of Chemical Physics 57(11): 4814-4820.

New et al. (1990). Liposomes. A Practical Approach. Oxford University Press. Pages 33-104).

The invention claimed is:

1. A process of preparing a stable liposomal preparation comprising a taxane, the process comprising:
   i) providing a stressed liposomal preparation comprising at least one saccharide, wherein liposomes of the stressed liposomal preparation comprise a cationic lipid and the stressed liposomal preparation comprises a positive zeta potential in about 0.05 M KCl solution at about pH 7.5 at room temperature, wherein an osmolar gradient is generated to provide the stressed liposomal preparation,
   ii) incubating the stressed liposomal preparation with a taxane, thereby obtaining a stressed liposomal preparation comprising a taxane incorporated into the liposomal membrane,
   iii) separating unsolubilised taxane from the stressed liposomal preparation, and
   iv) dehydrating by spray drying the stressed liposomal preparation to obtain a dehydrated liposomal preparation, and
   v) optionally, rehydrating the dehydrated liposomal preparation to obtain a stressed liposomal preparation, wherein the osmolar gradient maintains a stress on the liposomal preparation and stabilizes the taxane in the liposomal preparation and wherein the at least one saccharide is retained in the liposomes to maintain the osmolar gradient before and after rehydration.

2. The process according to claim 1, wherein the taxane is paclitaxel or a derivative thereof.

3. The process of claim 1, wherein separating unsolubilised taxane from the stressed liposomal preparation comprises filtration or centrifugation.

4. The process of claim 1, wherein the stressed liposomal preparation of step (ii) comprises DOTAP, DOPC, and paclitaxel.

5. The process of claim 4, wherein the stressed liposomal preparation of step (ii) comprises liposomes containing DOTAP, DOPC, and paclitaxel in a molar ratio of about 50:47:3.

6. The process of claim 1, wherein the saccharide is selected from mono-, di-, oligo- or poly-saccharides.

7. The process of claim 6, wherein the saccharide is trehalose.

8. The process of claim 1, further comprising rehydrating the dehydrated liposomal preparation comprising the taxane, wherein the rehydrated liposomal preparation comprises liposomes with homogeneous size distribution.

9. The process of claim 1, wherein one hour after rehydration, the liposomal preparation has a PI of less than 0.3, less than 0.25, or less than 0.20.

10. The process of claim 1, wherein the stressed liposomal preparation comprises a lower concentration of the saccharide in a free aqueous phase outside the liposomes as compared to a concentration of the saccharide encapsulated in an aqueous phase inside the liposomes.

11. The process of claim 1, wherein the osmolar gradient is generated by diluting the liposomal preparation with an aqueous medium to obtain the stressed liposomal preparation.

12. The process of claim 1, wherein the osmolar gradient is generated by dialyzing the liposomal preparation against an aqueous medium to obtain the stressed liposomal preparation.

13. The process of claim 1, wherein a range of the osmolar gradient maintaining the stress on the liposomal preparation is a concentration difference of between about 5% to about 30% (w/w).

* * * * *